United States Patent
Sun et al.

(10) Patent No.: US 10,010,584 B2
(45) Date of Patent: *Jul. 3, 2018

(54) TREATMENT OF DEPRESSIVE DISORDERS

(71) Applicant: Blanchette Rockefeller Neuroscience Institute, Morgantown, WV (US)

(72) Inventors: Miao-Kun Sun, Gaithersburg, MD (US); Daniel L Alkon, Bethesda, MD (US)

(73) Assignee: West Virginia University, Morgantown, WV (US)

( * ) Notice: Subject to any disclaimer, the term of this patent is extended or adjusted under 35 U.S.C. 154(b) by 341 days.

This patent is subject to a terminal disclaimer.

(21) Appl. No.: 13/669,353

(22) Filed: Nov. 5, 2012

(65) Prior Publication Data

US 2013/0165375 A1    Jun. 27, 2013

Related U.S. Application Data

(63) Continuation of application No. 13/152,616, filed on Jun. 3, 2011, now abandoned, which is a continuation of application No. 11/802,724, filed on May 24, 2007, now Pat. No. 7,977,377, which is a continuation-in-part of application No. 10/594,420, filed as application No. PCT/US2005/017158 on May 18, 2005.

(60) Provisional application No. 60/571,892, filed on May 18, 2004.

(51) Int. Cl.

| | | |
|---|---|---|
| A61K 31/335 | (2006.01) | |
| A61K 31/351 | (2006.01) | |
| A61K 31/357 | (2006.01) | |
| A61K 31/366 | (2006.01) | |
| A61K 38/18 | (2006.01) | |
| A61K 31/045 | (2006.01) | |
| A61K 31/05 | (2006.01) | |
| A61K 31/192 | (2006.01) | |
| A61K 31/196 | (2006.01) | |
| A61K 31/365 | (2006.01) | |
| A61K 31/4164 | (2006.01) | |
| A61K 31/4172 | (2006.01) | |

(52) U.S. Cl.
CPC ........ *A61K 38/1825* (2013.01); *A61K 31/045* (2013.01); *A61K 31/05* (2013.01); *A61K 31/192* (2013.01); *A61K 31/196* (2013.01); *A61K 31/365* (2013.01); *A61K 31/366* (2013.01); *A61K 31/4164* (2013.01); *A61K 31/4172* (2013.01)

(58) Field of Classification Search
CPC .. A61K 31/335; A61K 31/351; A61K 31/357; A61K 31/366

See application file for complete search history.

(56) References Cited

U.S. PATENT DOCUMENTS

| | | |
|---|---|---|
| 4,560,774 A | 12/1985 | Pettit et al. |
| 4,611,066 A | 9/1986 | Pettit et al. |
| 4,833,139 A | 5/1989 | Martin |
| 4,833,257 A | 5/1989 | Pettit et al. |
| 5,072,004 A | 12/1991 | Pettit |
| 5,075,338 A | 12/1991 | Knoll et al. |
| 5,196,447 A | 3/1993 | Pettit et al. |
| 5,220,068 A | 6/1993 | Knoll et al. |
| 5,288,514 A | 2/1994 | Ellman |
| 5,359,115 A | 10/1994 | Campbell et al. |
| 5,362,899 A | 11/1994 | Campbell |
| 5,393,897 A | 2/1995 | Pettit et al. |
| 5,430,053 A | 7/1995 | Pettit |
| 5,444,053 A | 8/1995 | Birkmayer |
| 5,545,636 A | 8/1996 | Health et al. |
| 5,578,590 A | 11/1996 | Grunicke et al. |
| 5,580,748 A | 12/1996 | Alkon et al. |
| 5,625,232 A | 4/1997 | Numata et al. |
| 5,770,593 A | 6/1998 | Grunicke et al. |
| 5,891,870 A | 4/1999 | Driedger et al. |
| 5,891,906 A | 4/1999 | Driedger et al. |
| 5,944,021 A | 8/1999 | Rodriguez |
| 5,955,501 A | 9/1999 | Driedger et al. |
| 5,962,498 A | 10/1999 | Driedger et al. |
| 5,962,504 A | 10/1999 | Kozikowski et al. |
| 5,972,684 A | 10/1999 | Bandman et al. |
| 5,981,165 A | 11/1999 | Brent et al. |
| 6,043,270 A | 3/2000 | Driedger et al. |
| 6,043,283 A | 3/2000 | Guillan |
| 6,080,582 A | 6/2000 | Alkon et al. |
| 6,080,784 A | 6/2000 | Driedger et al. |
| 6,187,568 B1 | 2/2001 | Nishida et al. |
| 6,242,479 B1 | 6/2001 | Wechter |
| 6,407,058 B1 | 6/2002 | Staddon et al. |
| 6,458,373 B1 | 10/2002 | Lambert et al. |
| 6,624,189 B2 | 9/2003 | Wender et al. |
| 6,825,229 B2 | 11/2004 | Etcheberrigaray et al. |
| 7,803,400 B2 | 9/2010 | Nelson et al. |
| 7,977,377 B2 | 7/2011 | Sun et al. |

(Continued)

FOREIGN PATENT DOCUMENTS

| | | |
|---|---|---|
| CA | 2401452 | 3/2003 |
| DE | A-3827974 | 2/1990 |

(Continued)

OTHER PUBLICATIONS

Cochinov, "Depression in cancer patients", Lancet Oncol 2001: 2: 499-505.*

(Continued)

*Primary Examiner* — Sahar Javanmard
(74) *Attorney, Agent, or Firm* — Finnegan, Henderson, Farabow, Garrett & Dunner, LLP

(57) ABSTRACT

The invention provides for the use of carbonic anhydrase activators; protein kinase C activators and FGF-18 to treat depressive disorders. The invention also relates to improved animal models and methods for screening and identifying compounds to treat depressive disorders.

9 Claims, 4 Drawing Sheets

(56) References Cited

U.S. PATENT DOCUMENTS

| | | |
|---|---|---|
| 2002/0193360 A1 | 12/2002 | Villalobos |
| 2003/0050302 A1 | 3/2003 | Etcheberrigaray |
| 2003/0077335 A1 | 4/2003 | Richardson et al. |
| 2003/0171356 A1 | 9/2003 | Etcheberrigaray et al. |
| 2003/0171385 A1 | 9/2003 | Alkon et al. |
| 2005/0037984 A1 | 2/2005 | Etcheberrigaray et al. |
| 2005/0065205 A1 | 3/2005 | Alkon |
| 2005/0075393 A1 | 4/2005 | Tomoyuki |

FOREIGN PATENT DOCUMENTS

| | | |
|---|---|---|
| DE | 19943198 | 3/2001 |
| EP | 0 115 472 | 8/1984 |
| EP | 0 324 574 A2 | 7/1989 |
| EP | 0 387 867 A1 | 9/1990 |
| EP | 0 413 191 A1 | 2/1991 |
| EP | 0 432 856 | 6/1991 |
| EP | 1 195 159 | 4/2002 |
| JP | 06-279311 | 10/1994 |
| JP | 2001-240581 | 9/2001 |
| JP | 2003-146883 | 5/2003 |
| RO | 86 393 A | 3/1985 |
| RU | 2115653 A | 7/1998 |
| WO | WO 85/03869 A1 | 9/1985 |
| WO | WO 91/07087 | 5/1991 |
| WO | WO 92/10092 | 6/1992 |
| WO | WO 93/09668 | 5/1993 |
| WO | WO 93/20242 | 10/1993 |
| WO | WO 94/08051 | 4/1994 |
| WO | WO 96/35417 | 11/1996 |
| WO | WO 97/43268 | 11/1997 |
| WO | WO 98/11923 | 3/1998 |
| WO | WO 98/32464 A1 | 7/1998 |
| WO | WO 2000/040241 | 7/1998 |
| WO | WO 99/08681 | 2/1999 |
| WO | WO 99/52519 | 10/1999 |
| WO | WO 99/59597 | 11/1999 |
| WO | WO 2000/066617 | 11/2000 |
| WO | WO 2001/83449 | 8/2001 |
| WO | WO 2001/68137 | 9/2001 |
| WO | WO 2001/93744 A2 | 12/2001 |
| WO | WO 2001/93883 | 12/2001 |
| WO | WO 2002/086106 | 1/2002 |
| WO | WO 2002/39998 | 5/2002 |
| WO | WO 2002/50013 A1 | 6/2002 |
| WO | WO 2002/083877 | 10/2002 |
| WO | WO 2002/097423 A3 | 10/2002 |
| WO | WO 2003/075850 A2 | 9/2003 |
| WO | WO 2003/075930 A1 | 9/2003 |
| WO | WO 2004/004641 A2 | 1/2004 |
| WO | WO 2004/047857 | 6/2004 |
| WO | WO 2005/032474 A2 | 4/2005 |
| WO | WO 2005/115548 A2 | 12/2005 |
| WO | WO 2006/031337 A2 | 3/2006 |
| WO | WO 2007/016202 A1 | 2/2007 |
| WO | WO 2007/044094 A1 | 4/2007 |
| WO | WO 2008/013573 | 1/2008 |
| WO | WO 2008/100449 | 8/2008 |

OTHER PUBLICATIONS

Agranoff et al., "Actinomycin D Blocks Formation of Memory of Shock-Avoidance in Goldfish," Science, 158 (Dec. 22, 1967).
Alkon et al., Protein Synthesis Required for Long-Term Memory is Induced by PKC Activation on Days Before Associative Learning, Proc. Natl, Acad. Sci. USA, 102:16432-16437 (2005).
Alkon, D.L., "Calcium-mediated reduction of ionic currents: A biophysical memory trace." Science, vol. 226, pp. 1037-1045, 1984.
Bank et al., "Classical Conditioning Induces Long-Term Translocation of Protein Kinase C in Rabbit Hippocampal CA1 Cells", Proc. Natl. Acad. Sci. USA, 85:1988-1992 (Mar. 1988).
Bondy et al., "The PHA-Induced Calcium Signal in Lymphocytes is Altered After Blockade of K+-Channels in Alzheimer's Disease," J. Psychiat. Res., 30(3):217-227 (1996).
Burke et al., "Update on Alzheimer's Disease: Promising advances in Detection and Treatment," Postgraduate Medicine, 106(5) (1999).
Burry, R. W., "PKC Activators (Phorbol Ester or Bryostatin) Stimulate Outgrowth of NGF-Dependent Neurites in a Subline of PC12 Cells," Journal of Neurosciences Research, 53:214-222 (1998).
Buxbaum et al., "Evidence That Tumor Necrosis Factor a Converting Enzyme is Involved in Regulated a-Secretase Cleavage of the Alzheimer Amyloid Protein Precursor," The Journal of Biological Chemistry, 273(43):27765-27767 (1998).
Cavallaro "Memory-Specific Temporal Profiles of Gene Expression in the Hippocampus", PNAS, 99( 25):16279-16284 (Dec. 2002).
Connolly, "Fibroblast Models of Neurological Disorders: Fluorescence Measurement Studies," TIPS, 19:171-177 (1998).
Crow et al., "Inhibiton of Protein Synthesis Blocks Long-Term Enhancement of Generator Potentials Produced by One-Trail in Vivo Conditioning in Hermissenda", Proc. Natl. Acad. Sci. USA, 87:4490-4494 (Jun. 1990).
Crow et al., "Protein Synthesis-Dependent and mRNA Synthesis-Independent Intermediate Phase of Memory in Hermissenda," The American Physiological Society, Rapid Communication, 495-500 (1999).
English Translation for JP 2001-240581 (2012).
English-language Translation for JP 6-279311 dated Jun. 2008.
Epstein et al., "Time Windows for Effects of Protein Synthesis Inhibitors on Pavlovian Conditioning in Hermissenda: Behavioral Aspects", Neurobiology of Learning and Memory, 79:127-131 (2003).
Espacenet English Abstract for EP 0 115 472 (2012).
Espacenet English Abstract for JP 2003-146883 (2012).
Etcheberrigaray et al., "Calcium Responses are Altered in Fibroblasts from Alzheimer's Patients and Pre-symptomatic PS1 Carriers; A Potential Tool for Early Diagnosis," Alzheimer's Reports, 3(5&6):305:312 (2000).
Etcheberrigaray et al., "Therapeutic effects of PKC activators in Alzheimer's disease transgenic mice", PNAS, 01(30):11141-11146 (2004).
Ezzeddine et al., "Prolonged Habituation of the Gill-Withdrawal Reflex in Aplysia Depends on Protein Synthesis, Protein Phosphatase Activity, and Postsynaptic Glutamate Receptors," The Journal of Neuroscience, 23(29):9585-9594 (Oct. 22, 2003).
Farley et al., "Protein Kinase C Inhibitors Prevent Induction and Continued Expression of Cell Memory in Hermissenda Type B Photoreceptors", Proc. Natl. Acad. Sci. USA, 88:2016-2020 (Mar. 1991).
Favit et al., "Alzheimer's-specific effects of soluble β-amyloid on protein kinase C-and -degradation in human fibroblasts", Cell Biology, 95:5562-5567 (1998).
Final Office Action dated Nov. 23, 2010, in U.S. Appl. No. 11/802,842.
Final Office Action dated Mar. 5, 2009, in U.S. Appl. No. 10/933,536.
Final Office Action dated May 13, 2010, in U.S. Appl. No. 12/068,742.
Flexner et al., "Effect of Acetoxycyclohemimide and of an Acetoxycycloheximide-Puromycin Mixture on Cerebral Protein Synthesis and Memory in Mice," Proc. N.A.S., 55:369-374 (1966).
Govoni et al., "Cytosol Protein Kinase C Downregulation in Fibroblasts from Alzheimer's Disease Patients," Neurology, 43:2581-2586 (1993).
Gundlfinger et al., "Different Regulation of Purkinje Cell Dendritic Development in Cerebellar Slice Sultures by Protein Kinase Calpha and -beta," Journal of Neurobiology, 57(1):95-109 (Oct. 2003).
Huynh et al., "Reduces Protein Kinase C Immunoreactivity and Altered Protein Phosphorylation in Alzheimer's Disease Fibroblasts," Arch Neurol 46 (1989).
Hyden et al., "Brain-Cell Protein Synthesis Specifically Related to Learning", Proceedings of the National Academy of Sciences, 65(4):898-904, (Apr. 1970).

(56) References Cited

OTHER PUBLICATIONS

Ibarreta et al., "Benzolactam (BL) Enhances sAPP Secretion in Fibroblasts and in PC12 Cells," Ageing, 10(5):1035-1040 (1999).
Ishii et al., "Protein Kinase C Activation and its Role in the Development of Vascular Complications in Diabetes Mellitus," J. Mol. Med., 76:21-31 (1998).
Jin et al., "Changes in Protein Kinases in Brain Aging and Alzheimer's Disease," Drugs &Aging, 6(2):136-149 (1995).
Kanno et al., "The Linoleic Acid Derivative DCP-LA Selectively Activates PKC-ϵ, Possibly Binding to the Phosphatidylserine Binding Site," Journal of Lipid Research, 47:1146-56 (2006).
Kanno et al., "The Newly Synthesized Linoleic Acid Derivative DCP-LA Selectively Activates PKC-ϵ", Dept. of Physiology, Hyogo College of Med., Hyogo, Japan, p. 552 (2006).
Khan et al., "An Internally Controlled Perifpheral Biomarker for Alzheimer's Disease: Erk1 and Erk2 responses to the Inflammatory Signal Bradykinin," PNAS, vol. 103, No. 35, pp. 13203-13207, Aug. 29, 2006.
Kuzirian et al., "Bryostatin and lactacystin affect PKC activation and long-term memory," Database Biosis [Online], Biosciences Information Service, Mar. 2006, Abstract.
Kuzirian et al., "Bryostatin Enhancement of Memory in Hermissenda", Biol. Bull, 210:201-214 (Jun. 2006).
Kuzirian et al., "Pavlovian Conditioning-Specific Increases of the Ca2+- and GTP-Binding Protein, Calexcitin in Identified Hermissenda Visual Cells", Journal of Neurocytology, 30:993-1008 (2001).
Lamberti et al., "Antideppressant-like effects of endogenous histamine and of two histamine H1 receptor agonists in the mouse forced swim test", British Journal of Pharmacology, Nature Publishing Group, Basingstoke, Hants; GB, vol. 123, No. 7, Jan. 1, 1998, pp. 1331-1336.
Lee et al., "Ubiquitination of Protein Kinase C-a and Degradation by the Proteasome," J. Biol. Chem., vol. 271, No. 35, pp. 20973-27976, Jun. 3, 1996.
Leontieva et al., "Identification of Two Distinct Pathways of Protein Kinase Ca Down-regulation in Intestinal Epithelial Cells", The Journal of Biological Chemistry, 279(7):5788-5801 (2004).
Lu et al., "Activation of Protein Kinase C Triggers Its Ubiquitination and Degradation," Molecular and Cellular Biology, 18(2): 839-845 (Feb. 1983).
Lyketsos, "Treating Depression in Alzheimer Disease, Efficacy and Safety of Sertraline Therapy, and the Benefits of Depression Reduction: The DIADS", Arch Gen Psychiatry, 2003, 60, pp. 737-746.
Martin et al., "Role of vitamin E and C on neurodegenerative diseases and cognitive performance," Nutrition Review vol. 60, No. 11, pp. 308-326 (2002).
Masliah, "Protein Kinase C Alteration is an Early Biochemical Marker in Alzheimer's Disease," The Journal of Neuroscience, 11(9): 2759-2767 (1991).
McPhie et al., "Cell Specificity of Molecular Changes During Memory Storage", Journal of Neurochemistry, 60( 2):646-651 (1993).
Mutter et al., "Chemistry and Clinical Biology of the Bryostatins," Bioorganic & Medicinal Chemistry, 8:1841-1860 (2000).
Nagata et al., "FR236924, a Newly Synthesized Derivataive of Linoleic Acid, Ameliorates Memory Deficits in Rats Intraventricularly Injected with Amyloid-Beta Peptide." Jpn. J. Physiol. 53, Suppl. 2003(319): S261.
Nagata et al., "The Newly Synthesized Linoleic Acid Derivative, CP-LA Ameliorates Memory Deficits in Animal Dmodels Treated with Amyloid-β Peptide and Scopolamine", Psychogeriatrics, 5:22-126 (2003).
Nelson et al., "Isolation of a G Protein That is Modified by Learning and Reduces Potassium Currents in Hermissenda," Science, 247:1479-1483 (Mar. 23, 1990).
Nelson et al., "Specific High Molecular Weight mRNAs induced by Associative Learning in Hermissenda", Proc. Nat. Acad. Sci. USA, 87:269-273 (Jan. 1990).
NME Digest; Drug News Perspect, 2002, pp. 666-674, vol. 15, No. 10.

Office Action (Restriction Requirement) dated Aug. 10, 2010, in U.S. Appl. No. 11/802,723.
Office Action (Restriction Requirement) dated Jun. 28, 2010, in U.S. Appl. No. 11/698,953.
Office Action dated Jan. 30, 2008, in U.S. Appl. No. 10/933,536.
Office Action dated May 26, 2010, in U.S. Appl. No. 11/802,842.
Office Action dated May 28, 2008, in U.S. Appl. No. 10/933,536.
Office Action dated May 9, 2011, in U.S. Appl. No. 10/476,459.
Office Action dated Sep. 18, 2012, in U.S. Appl. No. 13/042,892.
Office Action dated Sep. 5, 2012, in U.S. Appl. No. 12/538,245.
Office Action (Restriction Requirement) dated Jun. 23, 2009, in U.S. Appl. No. 12/068,742.
Office Action (Restriction Requirement) dated Mar. 7, 2011, in U.S. Appl. No. 10/594,420.
Office Action dated Aug. 15, 2011, in U.S. Appl. No. 10/594,420.
Office Action dated Feb. 4, 2010, in U.S. Appl. No. 11/802,842.
Office Action dated Jan. 31, 2012, issued in U.S. Appl. No. 12/851,222.
Office Action dated Jul. 20, 2011, in U.S. Appl. No. 11/802,723.
Office Action dated Jul. 7, 2011, in U.S. Appl. No. 11/698,953.
Office Action dated May 22, 2013, in U.S. Appl. No. 13/561,770.
Office Action dated May 4, 2012, in U.S. Appl. No. 13/152,616.
Office Action dated Oct. 21, 2009, in U.S. Appl. No. 12/068,742.
Olds et al., "Discrimination Learning Alters the Distribution of Protein Kinase C in the Hippocampus of Rats," The Journal of Neurosciences, 10(11 ):3707-3713 (Nov. 1990).
Olds et al., "Imaging of Memory-Specific Changes in the Distribution of Protein Kinase C in the Hippocampus", Science, 245:866-869 (Aug. 25. 1989).
Partial European Search Report EP 12005992.8, dated Jan. 31, 2013, 8 pages.
PKC Lab, pp. 1-4, 2010, retrieved from: http://www.pkclab.org/PKC/PKCbiology/PKCbiology_PKC_activators.htm.
Prevostel et al., "Protein Kinase Ca Actively Downregulates Through Caveolae-Dependent Traffic to an Endosomal Compartment," Journal of Cell Science, 113:2575-2584 (2000).
Protein Kinase C, pp. 1-6, 2010, retrieved from: http://en.wikipedia.org/wiki/Protein_kinase_C.
Quattrone et al., "Posttranscriptional Regulation of Gene Expression in Learning by the Neuronal ELAV-Like mRNA-Stabilizing Proteins", PNAS, vol. 98, No. 20, pp. 11668-11673, Sep. 25, 2001.
Sano et al., "A Controlled Trial of Selegiline, Alpha-Tocopherol, or Both as Treatment for Alzheimer's Disease", New England Journal of Medicine, pp. 1216-1222, Apr. 24, 1997.
Schrenk et al., "Alterned Dendritic Development of Cerebellar Purkinje Cells in Slice Cultures from Protein Kinase Cgamma-deficient Mice," Neuroscience 2002, 110(4):675-689 (2002).
Scioletti et al., "Memory Enhancement by Bryostain in Hermissenda", Biol. Bull., 207, (Oct. 2004) p. 159.
Smith et al., "Inhibition of the proteasome converts bryostatin from an antagonist to an agonist of protein kinase C (PKC)," FASEB Journal, Fed. of American Soc. for Experimental Biology, US, vol. 11. No. 9, Jan. 1, 1997, p. A987.
Sun et al., "Depressed or Demented: Common CNS Drug Targets?!", Current Drug Targets—CNS & Neurological Disorders 2002, 1, 575-592.
Sun et al., "Synergistic Effects of Chronic Bryostatin-1 and Alpha-tocopherol on Spatial Learning and Memory," Eur. J. Pharmacol., 584:328-337 (2008).
Talk et al., "Neurophysiological Substrates of Context Conditioning in Hermissenda Suggest a Temporally Invariant Form of Activity-Dependent Neuronal Facilitation", Neurobiology of Learning and Memory 72:95-117 (1999).
Tanaka et al., "The Newly Synthesized Linoleic Acid Derivative FR236924 Induces a Long-Lasting Facilitation of 4 Hippocampal Neurotransmission by Targeting Nicotinic Acetylcholine Receptors", Bioorganic & Medicinal Chem. Letters, 13:1037-1040 (2003).
Tanzi et al., "The Gene Defects Responsible for Familial Alzheimer's Disease," Neurobiology of Disease, 3:159-168 (1996).
Wender et al., "Function Oriented Synthesis: The Design, Synthesis, PCK Binding and Translocation Activity of a New Bryostatin Analog," 1 Curr. Drug Disc. Tech. 1 (2004).

(56) References Cited

OTHER PUBLICATIONS

Wender, "Role of the A-Ring of Bryostatin Analogues in PKkC Binding: Synthesis and Initial Biological Evaluation of New A-Ring Modified," Bryologs. Organic Letters, 7(10):1995-1998 (2005).
Wilkinson et al., "Research Communication: Isoenzyme specificity of bisindolylmaleimides, selective inhibitors of protein kinase C", Biochem. J. (1993) 294, 335-337.
Yaguchi et al., "Effects of Cis-unsaturated Free Fatty Acids on PKC-ε Activation and Nicotinic ACh Receptor Responses", Molecular Brain Res., 133:320-324 (2005).
Yaguchi et al., "Linoleic Acid Derivative DCP-LA Improves Learning Impairment in SAMP8", Neuropharmacology and Neurotoxicology, 17(1):105-108 (Jan. 23, 2006).
Yamamoto et al., "The Linoleic Acid Derivative FR236924 Facilitates Hippocampal Synaptic Transmission by Enhancing Activity of Presynaptic α7 Acetylcholine Receptors on the Glutamatergic Terminals", Neuroscience, 130:207-213 (2005).
Zhang et al., "Preclinical Pharmacology of the Natural Product Anticancer Agent Bryostatin 1, an Activator of Protein Kinase C1," Cancer Research, 56:802-808 (1996).
Zhao et al., "Brain Insulin Receptors and Spatial Memory—Correlated Changes in Gene Expression, Tyrosine Phosphorylation, and Signaling Molecules in the Hippocampus of Water Maze Trained Rats," The Journal of Biological Chemistry, 274(49):34893-34902 (1999).
Zhao et al., "Spatial learning induced changes in ecpression of the ryanodine type II receptor in the rat hippocampus," The FASEB Journal, vol. 14, pp. 290-300, Feb. 2000.
Abramets et al., "Behavioral Depression-Related Modifications of the Properties of Glutamatergic Synapses in the Basolateral Amygdalar Nucleus in Rats," Neurophysiology,34(4):283-293 (2002).
Barbas et al., "Multiple Serotonergic Mechanisms Contributing to Sensitization in Aplysia: Evidence of Diverse Serotonin Receptor Subtypes," Serotonin & Memory/Review, 10:373-386 (2003).
Battaini, "Protein Kinase C Isoforms as Therapeutic Targets in Nervous System Disease States," Pharmacological Research, 44(5):353-361 (2001).
Berke et al., "Dopamine and Glutamate Induce Distinct Striatal Splice Forms of Ania-6, an RNA Polymerase II-Associated Cyclin," Neuron, 32:277-287 (Oct. 25, 2001).
Berman et al., "Specific and Differential Activation of Mitogen-Activated Protein Kinase Cascades by Unfamiliar Taste in the Insular Cortex of the Behaving Rat," The Journal of Neuroscience, 18(23):10037-10044 (Dec. 1, 1998).
Besag, "Behavioral Effects of the New Anticonvulsants," Drug Safety, 24(7):513-536 (2001).
Birkmayer, "L-Deprenyl Plus L. Phenylalanine in the Treatment of Depression," Journal of Neural Transmission, 59:81-87 (1984).
Bouron et al. "Acute Application of the Tricyclic Antidepressant Desipramine Presynaptically Stimulates the Exocytosis of Glutamate in the Hippocampus," Neurosciece, 90(3):729-736, (1999).
Calo et al., "Pharmacology of Nociceptin and its Receptor: a Novel Therapeutic Target", British Journal of Pharmacology, 129:1261-1283 (2000).
Casini et al., "Carbonic Anhydrase Activators. The Selective Serotonin Reuptake Inhibitors Fluoxetine, Sertraline and Citalopram are Strong Activators of Isozymes I and II," Bioorganic & Medicinal Chemistry Letters, 13:2765-2766 (2003).
Cavalloaro et al., "Late Memory-Related Genes in the Hippocampus Revealed by RNA Fingerprinting", Proc. Natl. Acad. Sci. USA, 94:9669-9673 (Sep. 1997).
Chetkovich et al., "N-Methyl-D-Aspartate Receptor Activation Increases cAMP Levels and Voltage-Gated Ca2+ Channel Activity in Area CA1 of Hippocampus", Proc. Natl. Acad. Sci. USA, 88:6467-671 (Aug. 1991).
Coull et al., "Altered Brain Protein Kinase C in Depression: a Post-Mortem Study," European Neuropsychopharmacology, 10:283-288 (2000).
Davis, "The Mitogen-activated Protein Kinase Signal Transduction Pathway," The Journal of Biological Chemistry, 268(20):14553-14556 (Jul. 15, 1993).
English Abstract for RO 86393 dated Mar. 30, 1986, Derwent WPI.
English Abstract for RU 2115653 dated Dec. 27, 1995, Derwent WPI.
European Search Report for EP 0574 9738 dated Sep. 28, 2007.
European Search Report for EP 08 01 0738, dated Feb. 11, 2010.
Ferrari, "Behavioural Pharmacology of Imidazole, a Potential Antidepressant Agent," Arch. Int. Pharmacodyn, 277:303-312 (1985).
Gomez et al., "Ca2+ Signaling via the Neuronal Calcium Sensor-1 Regulates Assciative Learning and Memory in C. elegans," Neuron, 30:241-248 (Apr. 2000).
Gould et al., "Signaling Networks in the Pathophysiology and Treatment of Mood Disorders," Journal of Psychosomatic Research, 53:687-697 (2002).
Hahn et al., "Abnormalities in Protein Kinase C Signaling and the Pathphysiology of Bipolar Disorder," Bipolar Disorders, 2:81-86 (1999).
Hayes, "Acetozolamide in Bipolar Affective Disorders," Annals of Clinical Psychiatry, 6(2):91-98 (1994).
Hu et al., "FGF-18, a Novel Member of the Fibroblast Growth Factor Family, Stimulates Hepatic and Intestinal Proliferation," Molecular and Cellular Biology, 18(10):6063-6074 (Oct. 1998).
Hu et al., "Human Fibroblast Growth Factor-18 Stimulates Fibroblast Cell Proliferation and is Mapped to Chromosome 14p11", Oncogene, 18:2635-2642 (1999).
Impey et al., "Making New Connections: Role of ERK/MAP Kinase Signaling in Neuronal Plasticity", Neuron, 23:11-14 (May 1999).
International Preliminary Report on Patentability issued on PCT/US2005/017158, dated Jan. 16, 2007.
International Search Report for PCT/US2005/017158 dated Dec. 14, 2006.
Johnston Wilson et al., "Disease-specific Alterations in Frontal Cortex Brain Proteins in Schizophrenia, Bipolar Disorder, and Major Depressive Disorder," Molecular Psychiatry, 5:142-149 (2000).
Katzoff et al., "Nitric Oxide is Necessary for Multiple Memory Processes after Learning That a Food is Inedible in Aplysia," The Journal of Neurosciences, 22(21):9581-9594 (Nov. 1, 2002).
Kornhauser et al., "A Kinase to Remember: Dual Roles for MAP Kinase in Long-Term Memory", Neuron, 18:839-842 (Jun. 1997).
Kosik et al., "Microtubule-associated Protein 2: Monoclonal Antibodies Demonstrate the Selective Incorporation of Certain Epitopes into Alzheimer Neurofibrillary Tangles", Proc. Natl. Acad. Sci. USA, 81:7941-7945 (Dec. 1984).
Kravitz et al., "Dietary Supplements of Phenylalanine and Other Amino Acid Precursors of Brain Neuroamines in the Treatment of Depressive Disorders", Journal of the American Osteopathic Associate, 84(1 Suppl):119-123 (Sep. 1984).
Lenox et al., "Lithium and the Brain: A Psychopharmacological Strategy to a Molecular Basis for Manic Depressive Illness," Clin. Chem, 40(2):309-314 (1994).
Lieb et al., "Valproic Acid inhibits substance P-Induced Activation of Protein Kinase C Epsilon and Expression of the Substance P Receptor," Journal of Neurochemistry, 86:69-76 (2003).
Manji et al.. "Protein Kinase C Signaling in the Brain: Molecular Transduction of Mood Stabilization in the Treatment of Manic-Depressive Illness," Biol Psychiatry 46:1328-1351 (1099).
Manji et al., "Post-receptor Signaling Pathways in the Pathophysiology and Treatment of Mood Disorders," Mood Disorders, 481-489 (2000).
Mannisto et al., "Beneficial Effects of Co-administration of Catechol-O-Methyltransferase Inhibitors and L-dihydroxyphenylalanine in Rat Models of Depression", European Journal of Pharmacology, 274:229-233 (1995).
Masson et al., "Neurotransmitter Transporters in the Central Nervous System," Pharmacological Reviews, 51(3):436-464 (1999).
Mody et al., "Genome-wide gene expression profiles of the developing mouse hippocampus,", PNAS, 98(14):8862-8867 (Jul. 17, 2001).

(56) References Cited

OTHER PUBLICATIONS

Morishita et al., "Different Effect of Desipramine on Protein Kinase C in Platelets Between Bipolar and Major Depressive Disorders," Psychiatry and Clinical Neurosciences, 53:11-15 (1999).
Morshita et al., "Effects of Tricylic Antidepressants on Protein Kinase C Activity in Rabbit and Human Platelets in Vivo," Journal of Affective Disorders, 70:329-332 (2002).
Ohbayashi et al., "Structure and Expression of the mRNA Encoding a Novel Fibroblast Growth Factor, FGF-18," The Journal of Biological Chemistry, 273(29):18181-18164 (1998).
Pandey et al., "Protein Kinace C in Platelets of Depressed Patients," Biological Psychiatry, 44:909-911 (1998).
Pandey et al., "Protein Kinase C and Phospholipase C Activity and Expression of Their Specific Isozymes is Decreased and Expression of MARCKS is Increased in Platelets of Bipolar but Not in Unipolar Patients," Neuropschoparmacology, 26(2):216-228 (2002).
Partial European Search Report EP 08 01 0738, dated Oct. 13, 2009.
Pettit et al., "Antineoplastic Agents 224 Isolation and Structure of Neristatin 1," Journal of the American Chemical Society, 113(17):6893-6695 (1991).
Popoli et al., "Second Messenger-Regulated Protein Kinases in the Brain: Their Functional Role and the Action of Antidepressant Drugs," J. Neurochem.74(1):21-31 (2000).
Shelton, "Cellular Mechanisms in the Vulnerability to Depression and Response to Antidepressants," Depression, 23(4) (Dec. 2000).
Sun et al., "Carbonic Anhydrase Gating of Attention: Memory Therapy and Enhancement," TRENDS in Pharmacological Sciences, 23(2) (Feb. 2002), pp. 83-89.
Sun et al., "Dual Effects of Bryostatin-1 on Spatial Memory and Depression", Eur. J. Pharmacol., vol. 512, pp. 43-51, 2005.
Sun et al., "Functional Switching of GABAergic Synapses by Ryanodine Receptor Activation," Proc. Nat'l. Acad. Sci USA, 97:12300-12305 (2000).
Supuran et al., Carbonic Anhydrase Activators. XV. A Kinetic Study of Interaction of Bovine Isozyme II with Pyrazoles, Bis- and Tris-azolyl-methanes:, Biol. Pharm. Bull., 19(11):1417-1422 (1988).
Suzuki et al., "Altered 5-HT-Induced Calcium Response in the Presence of Staurosporine in Blood Platelets from Bipolar Disorder Patients," Neuropsychopharmacology, 28:1210-1214 (2003).
Tischmeyer et al., "Activation of Immediate Early Genes and Memory Formation", CMLS, Cell. Mol. Life Sci., 55:564-574 (1999).
Tsien et al., "The Essential Role of Hippocampal CA1 NMDA Receptor-Dependent Synaptic Plasticity in Spatial Memory," Cell, 87:1327-1338 (Dec. 27, 1996).
Vrontakis et al., "Current Drug Targets—CNS & Neurological Disorders. Glanain: A Biologically Active Peptide," 1(6):531-541 (2002).
Wang et al., "Flouxetine Depresses Glutamate Exocytosis in the Rat Cerebrocortical Nerve Terminals (Synaptosomes) via Inhibition of p/a Ca2+ Channels," SYNAPSE, 48:170-177 (2003).
Wang et al., "Increased Membrane-Associated Protein Kinase C Activity and Translocation in Blood Platelets from Bipolar Affective Disorder Patients," Journal of Psychiatric Research, 33:171-179 (1999).
Yamanouchi et al., "Early Forms of Microtubule-associated Protein are Strongly Expressed in Cortical Dysplasia", Acta Neuropathol, 95:466-470 (1998).
Yildiz, "Phosphoinositide metabolism, lithium and manic depresive illness," Spectroscopy 16:307-316 (2002).
Zhang et al., "Citron Binds to PSD-95 at Glutamatergic Synapses on Inhibitory Neurons in the Hippocampus," The Journal of Neuroscience, 19(1):96-108 (Jan. 1, 1999).
Zhen et al., "The p38 Mitogen-Activated Protein Kinase is Involved in Associative Learning in Rabbits," The Journal of Neuroscience, 2(15):5513-5519 (Aug. 1, 2001).
Alkon et al., "Reduction of two voltage-dependent K+ currents mediates retention of a learned association", Behav. Neural Biol., vol. 44, pp. 278-300, 1985.
Alkon et al., "Regulation of Hermissenda K+ Channels by Cytoplasmic and Membrane-Associated C-Kinase," J. Neurochem., 51(3):903-916 (1988).
Ashendel et al., "Protein Kinase Activity Associated With a Phorbol Ester Receptor Purified from Mouse Brain", Cancer Res., vol. 43, pp. 4333-4337, 1983.
Baltuch, G.H. et al., "Protein Kinase C Inhibitors Suppress Cell Growth in Established and Low-passage Glioma Cell Lines. A Comparison Between Staurosporine and Tamoxifen", Neurosurgery, Sep. 1993, vol. 33, No. 3, pp. 495-501.
Bennett et al., "Expression Analysis of BACE2 in Brain and Peripheral Tissues," The Journal of Biological Chemistry, 275(27):20647-20651 (2000).
Bergamaschi et al., "Defective Phorbol Ester-Stimulated Secretion of B-Amyloid Precursor Protein from Alzheimer's Disease Fibroblasts," Neuroscience Letters, 201:1-4 (1995).
Bergold et al., "Protein Synthesis During Acquisition of Long-Term Facilitation is Needed for the Persistent Loss of Regulatory Subunits of the Aplysia cAMP-Dependent Protein Kinase", Proc. Natl. Acad. Sci. USA, 87:3788-3791(May 1990).
Bhagavan et al., "Restoration of TEA-Induced Calcium Responses in Fibroblasts from Alzheimer's Disease Patients by a PKC Activator," Neurobiol. Disease, 5:177-187 (1998).
Blobe et al., "Regulation of protein kinase C and role in cancer biology," Cancer Metast. Rev. 1994; 13:411-431.
Budziszewska et al., "Antidepressant Drugs Inhibit Glucocorticoid Receptor-Mediated Gene Transcription—A Possible Mechanism," British Journal of Pharmacology, 130,1385-1393 (2000).
Bursell S.E. et al., "Can Protein Kinase C Inhibition and Vitamin E Prevent the Development of Diabetic Vascular Complications?", Diabetes Research and Clinical Practice, vol. 45, No. 2/03, Jan. 1999, pp. 169-182.
Cai et al., "BACE1 is the major β-secretase for Generation of Aβ Peptides by Neurons," Nature Neuroscience, 4(3):233-234 (Mar. 2001).
Calingasan et al., "Accumulation of Amyloid Precursor Protein-like Immunoreactivity in Rat Brain in Response to Thiamine Deficiency", Brain Research, Apr. 17, 1995, vol. 677, No. 1, p. 50.
Caputi et al., "Increased Secretion of the Amino-Terminal Fragment of Amyloid Precursor Protein in Brains of Rats with a Constitutive Up-Regulation of Protein Kinase C," J. Neurochem., 68(6):2523-2529 (1997).
Chaudhuri et al., "Fatigue in Neurological Disorders," The Lancet, 262:978-988 (2004).
Chow, C.K., "Vitamin E Regulation of Mitochondrial Superoxide Generation", Biological Signals and Receptors, vol. 10, No. 1-2, Jan. 2001, pp. 112-124.
Clamp et al., "The Clinical Developments of Bryostatins", Anti-Cancer Drugs, vol. 13, Issue 7, pp. 673-683, Aug. 2002.
Cole et al., "Decreased Levels of Protein Kinase C in Alzheimer Brain," Brain Research, 452:165-174 (1988).
Collin et al., "Sequential Modification of membrane currents induced by classical conditioning" Biophysical J. 54: 955-961, 1988.
Coughlan et al., "Factors Influencing the Processing and Function of the Amyloid B Precursor Protein—A Potential Therapeutic Target in Alzheimer's Disease?," Pharmacology & Therapeutics, 86:111-144 (2000).
De Lorenzo et al., "Bryostatin-1 Stimulates the Transcription of Cyclooxygenase-2: Evidence for an Activator Protein-1-Dependent Mechanism", Clinical Cancer Research, 9:5036-5043 (2003).
Desdouits et al., "Amyloid β Peptide Formation in Cell-free Preparations," The Journal of Biological Chemistry, 271(40):24670-24674 (1996).
Efthimiopoulos et al., "Intracellular Cyclic AMP Inhibits Constitutive and Phorbol Ester-Stimulated Secretory Cleavage of Amyloid Precursor Protein," J. Neurochem., 67(2):872-875 (1996).
Eriksen, "Linking Work Factors to Neck Myalgia: The Nitric Oxide/Oxygen Ratio Hypothesis", Medical Hypotheses 62:721-726 (2004).
Esler et al., "A Portrait of Alzheimer Secretases—New Features and Familiar Faces," Science, 293:1449-1454 (2001).

(56) References Cited

OTHER PUBLICATIONS

Etcheberrigaray et al., "Classical conditioning and protein kinase C activation regulate the same single potassium channel in Hermissenda crassicornis photoreceptors", Proc Natl Acad Sci USA, 89: 7184-8, 1992.
Extended European Search Report in 14001452.3 dated Jun. 30, 2014.
Extended European Search Report in 15002036.0 dated Nov. 2, 2015.
Extended European Search Report issued in EP 12002638 dated Jun. 19, 2012.
Extended European Search Report issued on EP 12005992.8 dated May 24, 2013.
Extended European Search Report, for EP Application No. 14001303.8 dated Nov. 21, 2014.
Gabuzda et al., "Inhibition of β-Amyloid Production by Activation of Protein Kinase C," J. Neurochem., 61(6):2326-2329 (1993).
Ghosh et al., "Design of Potent Inhibitors for Human Brain Memapsin 2 (β.-Secretase)," J. Am. Chem. Soc., 122(14):3522-3523 (2000).
Gillespie et al., "Secretory Processing of the Alzheimer Amyloid B/A4 Protein Precursor is Increased by Protein Phosphorylation," Biochemical and Biophysical Research Communications, 187(3):1285-1290 (1992).
Glazer, R.I., "Protein Kinase C in Multidrug Resistance, Neoplastic Transformation, and Differentiation", Protein Kinase C, New York Oxford Oxford University Press, pp. 171-198, (1994).
Goekjian, et al., "Protein Kinase C in the Treatment of Disease: Signal Transduction Pathways, Inhibitors, and Agents in Development," Current Medicinal Chemistry, 6:877-903 (1999).
Govoni et al., "Fibroblasts of Patients Affected by Down's Syndrome Oversecrete Amyloid Precursor Protein and are Hyporesponsive to Protein Kinase C Stimulation," Neurology, 47:1069-1075 (1996).
Haniu et al., "Characterization of Alzheimer's β-Secretase Protein BACE," The Journal of Biological Chemistry, 275(28):21099-21106 (2000).
Hardy, "Amyloid, the Presenilins and Alzheimer's Disease," TINS, 20(4): 154-159 (1997).
Hardy, "Molecular Genetics of Alzheimer's Disease," Acta Neurol Scand, Supplemental, 165:13-17 (1996).
Hennings et al., "Bryostatin 1, an activator of protein kinase C, inhibits tumor promotion by phorbol esters in SENCAR mouse skin," (1987) Carcinogenesis 8(9): 1343-46.
Hickman et al., "Bryostatin 1, A Novel Antineoplastic Agent and Protein Kinase C Activator, Induces Human Myalgia and Muscle Metabolic Defects: A P Magnetic Resonance Spectroscopic Study", British Journal of Cancer, 72:998-1003 (1975).
Hoelting et al., "12-0-tetradecanoyl-phorbol-β-acetate (TPA) Counteracts the Anti-Proliferative and Antiinvasive Effects of Tamoxifen in a Metastatic Follicular Thyroid Cancer Cell Line", Proc. Am. Cancer Res., Mar. 1995, vol. 36, Abstract No. 481.
Hofmann, "The Potential for Isoenzyme-Selective Modulation of Protein Kinase C," The FASEB Journal, 11:649-669 (1997).
House et al., "Protein kinase C contains a pseudosubstrate prototope in its regulatory domain." Science, vol. 238, No. 4834, pp. 1726-1728, Dec. 1987.
Howe, C. et al., "Differetial Effect of the Manipulation of Protein Kinase C Activity on Normal Versus Leukemic Progenitor Cell Response to rGM-CSF", Proc. Am. Assoc. Cancer Res., Mar. 1989, vol. 30, Abstract No. 244.
Hug et al., "Protein kinase C isoenzymes: divergence in signal transduction48 " Biochem J. 1993;291:329-343.
Hung et al., "Activation of Protein Kinase C Inhibits Cellular Production of the Amyloid β-Protein," The Journal of Biological Chemistry, 268( 31):22959-22962 (1993).
International Search Report and Written Opinion for PCT/US2005/028522 dated Apr. 13, 2006.
International Search Report and Written Opinion for PCT/US2008/006158 dated Apr. 9, 2009.
International Search Report and Written Opinion for PCTIUS2006/029110 dated Jan. 2, 2007.
International Search Report and Written Opinion for PCTIUS2007/002454 dated Jul. 13, 2007.
International Search Report for PCT/US2003/07101 dated Oct. 17, 2003.
Jayson et al., "A phase I trial of bryostatin 1 in patients with advanced malignancy using a 24 hour infusion." British Journal of Cancer, vol. 72, pp. 461-468, 1995.
Jolly-Tornetta et al., "Protein Kinase C Regulation of Intracellular and Cell Surface Amyloid Precursor Protein (APP) Cleavage in CH0695 Cells," Biochemistry, 39:15282-15290 (2000).
Jolly-Tornetta et al., Regulation of Amyloid Precursor Protein (APP) Secretion by Protein Kinase Cα in Human Ntera 2 Neurons (NT2N); Biochemistry, 39(25):7428-7435 (2000).
Katzman, "Alzheimer's disease," New England. Journal of Medicine. 1986;314:964-973.
Khalifah et al., Interaction of the Unique Competitive Inhibitor Imidazole and Related Compounds with the Active Site Metal of Carbonic Anhydrase: Linkage between pH Effects on the Inhibitor Binding Activity and pH Effects on the Visible Spectra of Inhibitor Complexes with the Cobalt-Substituted Enzyme, 1987, Biochemistry, vol. 26, pp. 7057-7063.
Kikkawa et al., "Calcium-activated, phospholipid-dependent protein kinase from rat brain. Subcellular distribution, purification, and properties." J. Biol. Chem. vol. 257, pp. 13341-13348, 1982.
Kikkawa et al., "The Protein Kinase C Family: Heterogeneity and its Implications." Ann. Rev. Biochem, vol. 58, pp. 31-44, 1989.
Kim et al, Amyloid Precursor Protein Processing is Separately Regulated by Protein Kinase C and Tyrosine Kinase in Human Astrocytes, Neurosci. Letters, 324(3):184-188 (May 2002).
Kinouchi et al., "Conventional Protein Kinase C (PKC)-α and Novel PKCϵ, But Not -δ, Increase the Secretion of an N-Terminal Fragment of Alzheimer's Disease Amyloid Precursor Protein from PKC cDNA Transfected 3Y1 Fibroblasts," FEBS Letters, 364:203-206 (1995).
Kogure, K. et al., "Alpha-Tocopheryl Succinate Activates Protein Kinase C in Cellular and Cell-free Systems", Journal of Nutritional Science and Vitaminology, Oct. 2003, vol. 49, No. 5, pp. 310-314.
Kozikowski et al., "Modeling, Chemistry, and Biology of the Benzolactam Analogues of Indolactam V (ILV). 2. Identification of the Binding Site of the Benzolactams in the CRD2 Activator-Binding Domain in PKCs and Discovery of an ILV Analogue of Improved Isozyme Selectivity," J. Med. Chem.,40:1316-1326 (1997).
Kunisaki et al., "Normalization of diacylglycerol-protein kinase C activation by vitamin E in aorta of diabetic rats and cultured rat smoth muscle cells exposed to elevated glucose levels." Diabetes, vol. 43, pp. 1372-1377, 1994.
Lee et al., "Dephosphorylation of activated protein kinase C contributes to downregulation by bryostatin," Am. Physiological Soc. 1996, C304-C311.
Li et al., "Endothelin Receptor Antagonist CPU0213 and Vitamin E Reverse Downregulation of FKBP12.6 and SERCA2a: A Role of Hyperphosphorylation of PKCϵ," European Journal of Pharmacology, 591:211-18 (2008).
Maiorini et al., "Potential Novel Targets for Alzheimer Pharmacotherapy: I. Secretase," Journal of Clinical Pharmacy and Therapeutics, 27:169-183 (2002).
Marshall et al., "Phase 1 Study of Prolonged Infusion Bryostatin-1 in Patients with Advanced Malignancies", Cancer Biology & Therapy 1:4, 409-416 (Jul./Aug. 2002).
Masliah et al., "Role of Amyloid Precursor Protein in the Mechanisms of Neurodegeneration in Alzheimer's Disease," Laboratory Investigation, 77(3):197-209 (1997).
Matsui et al., "The Role of Growth Factors in the Activity of Pharmacological Differentiation Agents," Cell Growth and Differentiation, 13(6) (Jun. 2002), pp. 275-283.
McKhann et al., "Clinical diagnosis of Alzheimer's disease: report of the NINCDS-ADRDA Work Group under the auspices of Department of Health and Human Services Task Force on Alzheimer's Disease", Neurology, vol. 34. No. 7, pp. 939-944, Jul. 1984.

(56) References Cited

OTHER PUBLICATIONS

McLoughlin et al., "Muscle Pains and Biochemical Changes Following Suxamethonium Administration After Six Pretreatment Regimens", Anaesthesia, 47:202-206 (1992).
Muscat et al., "Antidepressant-Like Effects of Dopamine Agonists in an Animal Model of Depression," Biol Psychiatry, vol. 31, 1992, pp. 937-946.
Namba, Y. et al., "Apolipoprotein E Immunoreactivity in Cerebral Amyloid Deposits and Neurofibrillary Tangles in Alzheimer's Disease and Kuru Plaque Amyloid in Creutzfeldt-Jakob Disease", Brain Research, Feb. 8, 1991, vol. 541, No. 1, pp. 163-166.
Nan et al., "Dual Function Glutamate-Related Ligands: Discovery of a Novel, Potent Inhibitor of Glutamate Carboxypeptidase II Possessing mGluR3 Agonist Activity," Journal of Medicinal Chemistry, 43(5):772-774 (2000).
Nishizuka, Y., "Studies and prospectives of the protein kinase C family for cellular regulation", Cancer, vol. 63, pp. 1892-1903, 1989.
Office Action (Final) dated Dec. 3, 2013, in U.S. Appl. No. 12/883,444.
Office Action (Final) dated Jun. 9, 2015, in U.S. Appl. No. 11/802,842.
Office Action (Final) dated Nov. 14, 2016, in U.S. Appl. No. 12/068,742.
Office Action dated Feb. 19, 2014, in U.S. Appl. No. 13/042,892.
Office Action dated Jun. 26, 2013, in U.S. Appl. No. 12/883,444.
Office Action dated Nov. 17, 2014, in U.S. Appl. No. 12/883,444.
Office Action (final) dated Jul. 13, 2015, in co-pending U.S. Appl. No. 12/883,444.
Office Action (final) dated May 5, 2016, U.S. Appl. No. 13/042,892.
Office Action (non-final) dated May 10, 2016, U.S. Appl. No. 12/068,742.
Office Action dated Feb. 1, 2016, U.S. Appl. No. 11/802,842.
Office Action dated Feb. 13, 2015, in U.S. Appl. No. 13/660,567.
Office Action dated Feb. 4, 2016, U.S. Appl. No. 13/851,161.
Office Action dated Jan. 10, 2014, in U.S. Appl. No. 12/068,742.
Office Action dated Jan. 24, 2014, in U.S. Appl. No. 13/851,161.
Office Action dated Jul. 16, 2013, in U.S. Appl. No. 11/802,842.
Office Action dated Jun. 1, 2016, in U.S. Appl. No. 14/196,455.
Office Action dated Mar. 16, 2015, in U.S. Appl. No. 12/068,742.
Office Action (final) dated Jun. 19, 2017, in U.S. Appl. No. 12/068,742.
Office Action dated Mar. 20, 2017, U.S. Appl. No. 11/802,842.
Office Action dated Nov. 30, 2016, U.S. Appl. No. 13/042,892.
Office Action dated Jul. 10, 2017, U.S. Appl. No. 13/042,892.
Office Action (Final) dated Aug. 31, 2016, in U.S. Appl. No. 11/802,842.
Office Action (Final) dated Aug. 29, 2017, in U.S. Appl. No. 11/802,842.
Office Action dated Aug. 26, 2016, in U.S. Appl. No. 14/222,922.
Office Action (final) dated Nov. 2, 2017, in U.S. Appl. No. 14/222,922.
Page et al., "A Short Preparation of an Advance Intermediate for Lactacystin Synthesis: The Complete Carbon Skeleton of Clasto-Lactacystin Dihydroxyacid," Synlett 2003, No. 7, pp. 1025-1027.
Rampello et al., "Dopamine and Depression: Therapeutic Implications, CNS," Drugs, vol. 13, No. 1, Jan. 1, 2000, p. 35-45.
Ricciarelli et al., Vitamin E: Protective Role of a Janus Molecule. The FASEB Journal, 15:2314-2315 (2005).
Robner et al., "Short Communication: Protein Kinase Cα and β1 Isoforms are Regulators of α-Secretary Proteolytic Processing of Amyloid Precursor Protein in Vivo," European Journal of Nueuroscience, 13:1644-1648 (2001).
Sanchez-Andres et al., "Voltage-clamp analysis of the effect of classical conditioning on the hippocampus", J Neurophysiol. 65: 796-807, 1991.
Savage et al., "Turnover of Amyloid β-Protein in Mouse Brain and Acute Reduction of Its Level by Phorbol Ester," The Journal of Neuroscience, 18(5):1743-1752 (1998).

Scheuner et al., "Secreted Amyloid β-Protein Similar to that in the Senile Plaques of Alzheimer's Disease is Increased in Vivo by the Presenilin 1 and 2 and APP Mutations linked to Familial Alzheimer's Disease," Nature Medicine, 2(8): 864-870 (1996).
Selkoe, "Alzheimer's Disease: Genes, Proteins, and Therapy," Physiological Reviews, 81(2):741-766 (2001).
Selkoe, "Normal and Abnormal Biology of the β-Amyloid Precursor Protein," Annu. Re. Neurosci., 17:489-517 (1994).
Selkoe, "Translating Cell Biology into Therapeutic Advances in Alzheimer's Disease," Nature, 399(24):A23-A31 (1999).
Shimohama et al., "Assessment of Protein Kinase C Isozymes by Two-Site Enzyme Immunoassay in Human Brains and Changes in Alzheimer's Disease," Neurology, 43:1407-1413 (1993).
Shoulson, "Experimental Therapeutics of Neurodegenerative Disorders: Unmet Needs," Science, 282:1072-1074 (1998).
Sinha et al., "Purification and Cloning of Amyloid Precursor Protein β-Secretase from Human Brain," Nature, 402:537-540, (1999).
Skovronsky et al., Protein Kinase C-Dependent α-Secretase Competes with β-Secretase for Cleavage of Amyloid-β Precursor Protein in the Trans-Golgi Network, The Journal of Biological Chemistry, 275(4):2568-2575 (2000).
Small et al., "Alzheimer's Disease and the Amyloid β. Protein: What is the Role of Amyloid?," Journal of Neurochemistry, 73(2):443-449 (1999).
St. George-Hyslop et al., "The genetic defect causing familial Alzheimer's disease maps on chromosome 21", Science vol. 235, No. 4791, pp. 885-890, Feb. 1987.
Supplemental Partial European Search Report for EP03742389 dated Sep. 12, 2007.
Supplementary European Search Report for EP03716386 (PCT/US2003/07101) dated Jun. 30, 2008.
Szallasi et al., "Differential Regulation of Protein Kinase C Isozymes by Bryostatin 1 and Phorbol 12-Myristate 13-Acetate in NIH 3T3 Fibroblasts," Journal of Biological Chemistry, 269(3):2118-2124 (1994).
Tanzi et al., "Protease Inhibitor domain encoded by an amyloid protein precursor mRNA associated with Alzheimer's disease," Nature, 1988; 331:528-530.
Tenovuo, "Pharmacological Enhancement of Cognitive and Behavioral Deficits after Traumatic Brain Injury," Curr. Op. Neur., 19:528-533 (2006).
Turner et al., "Specificity of Memapsin 1 and Its Implications on the Design of Memapsin 2 (β-Secretase) Inhibitor Selectivity," Biochemistry, 41:8742-8746 (2002).
U.S. Department of Health and Human Services Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 6, 2005, Pharmacology and Toxicology, 30 pages.
Varterasian et al., "Phase II Trial of Bryostatin 1 in Patients with Relapsed Low-Grade Non-Hodgkin's Lymphoma and Chronic Lymphocytic Leukemia," Clinical Cancer Research, vol. 6, pp. 825-828, 2000.
Vassar et al., Aβ-Generating Enzymes: Recent Advances in β and γ-Secretase Research, Neuron, 27:419-422 (2000).
Vassar et al., "β-Secretase Cleavage of Alzheimer's Amyloid Precursor Protein by the Transmembrane Aspartic Protease BACE," Science, 286:735-741 (1999).
Wang et al., "Attenuated Protein Kinase C Activity and Translocation in Alzheimer's Disease Brain," Neurobiology of Aging, 15(3):293-298 (1994).
Wang et al., "Neuroprotection Targets After Traumatic Brain Injury," Curr. Op. Neur., 19:514-519 (2006).
Webb et al., "Protein Kinase C Isoenzymes: A Review of Their Structure, Regulation and Role in Regulating Airways Smooth Muscle Tone and Mitogenesis," British Journal of Pharmacology, vol. 130, pp. 1433-1452, 2000.
Weitman et al., "A Phase I Trial of Bryostatin-1 in Children with Refractory Solid Tumors: A Pediatric Oncology Group Study", Clinical Cancer Research, vol. 5, pp. 2344-2348, 1999.
Wender et al., "The Design, Computer Modeling, Solution Structure, and Biological Evaluation of Synthetic Analogs of Bryostatin I," Proc. Natl. Acad. Sci., 95:6624-6629 (Jun. 1998).

(56) References Cited

OTHER PUBLICATIONS

Wender et al., "Total Synthesis and Initial Biological Evaluation of New B-Ring Modified Bryostatin Analogs," [[8]] Org Lett. 8:5299-5302 (Oct. 20, 2006).

Wiltfang et al., "Molecular Biology of Alzheimer's Dementia and Its Clinical Relevance to Early Diagnosis and New Therapeutic Strategies," Gerontology, 47:65-71 (2001).

Woolf et al., "Hippocampal Microtubule-associated Protein-2 Alterations with Contextual Memory", Brain Research, 821(1):241-249 (Mar. 6, 1999).

Xu et al., "Metabolism of Alzheimer β-Amyloid Precursor Protein; Regulation by Protein Kinase A in Intact Cells and in a Cell-Free System," Proc. Natl. Acad. Sci. USA, 93:4081-4084 (1996).

Yamada, K. et al., "Protective Effects of Idebenone and Alpha-tocopherol on Beta-amyloid-(1-42)-induced Learning and Memory Deficits in rats: Implication of Oxidative Stress in Beta-amyloid-induced Neurotoxicity in vivo", Jan. 1999, vol. 11, No. 1, pp. 83-90.

\* cited by examiner (A)

(B)

TREATMENT OF DEPRESSIVE DISORDERS

This is a continuation of U.S. application Ser. No. 13/152,616, filed Jun. 3, 2011, which is a continuation of U.S. application Ser. No. 11/802,724, now U.S. Pat. No. 7,977,377, filed May 24, 2007, which is a continuation-in-part of U.S. patent application Ser. No. 10/594,420 that was filed on May 18, 2005, which is a 371 national stage application based on International Application No. PCT/US2005/017158 that was filed on May 18, 2005, which claims the benefit of U.S. Provisional Application No. 60/571,892, filed May 18, 2004, all of which are incorporated herein by reference in their entireties.

FIELD OF THE INVENTION

The present invention relates to the treatment of depressive disorders with compounds that improve learning and memory. Specifically, the invention relates to the fields of carbonic anhydrase activators, protein kinase C activators and fibroblast growth factors as pharmaceutical agents in the treatment of depressive disorders. The present invention also relates to the field of animal models for depressive disorders.

BACKGROUND OF THE INVENTION

A. Depression and Traditional Treatment

Depression is one of the most prevalent and pervasive forms of mental illness that affects individuals across age and gender lines. (Gainotti et al. (2001) *J. Neural Neurosurg. Psychiatr.* 71: 258-261; Wong et al. (2001) *Nature Rev. Neurosci.* 2: 343-351; Nestler et al. (2002) *Neuron* 34: 13-25). The lifetime risk of major depression is about 12% in men and about 25% in women, generally, (Kessler et al. (1994) *Arch. Gen. Psychiatry* 51: 8). In addition, about 5 to 10% of all patients in the primary care environment, present with major depression, whereas about 3 to 5% of patients are diagnosed with dysthymia. (Barrett et al. (1988) *Arch. Gen. Psychiatry* 45: 1100). In an in-patient setting, however, between 10 and 14% of all patients are diagnosed with major depression. (Blackburn et al. (1997) *Br. J. Psychiatry* 171: 328). Major depression is a particularly disabling and pernicious, in part, because it is recurring. The rate of relapse for patients with major depression is about 40% over a two-year period after a first episode. The occurrence of relapse increases to about 75% within a five year period after the diagnosis of a second episode of major depression. (Solomon et al. (2000) *Am. J. Psychiatry* 157: 229).

Depressive disorders are most commonly treated with three main classes of compounds: 1) monoamine oxidase inhibitors; 2) heterocyclic antidepressants; and 3) selective serotonin reuptake inhibitors (SSRIs). The known and currently prescribed antidepressants are by numerous side effects. Monoamine oxidase inhibitors were the first class of antidepressants used clinically. Monoamine oxidase inhibitors, including isocarboxazid, phenelzine, and tranylcypromine, inhibit the metabolism of phenylethylamine and catabolism of dopamine, serotonin and norepinephrine. As a consequence of numerous dietary restrictions associated with the use of monoamine oxidase inhibitors, extensive side effects, including hypertension, headache, myoclonic jerk, sleep disruption, and gastrointestinal complications, monoamine oxidase inhibitors are currently not used as a first-line antidepressant. The tricyclic antidepressants, including, imipramine, desipramine, nortrypline, amitrypline, doxepin and protrypline, produce a variety of anticholinergic side effects, drowsiness, orthostatic hypotension, cardiac arrhythmias and weight gain. Although generally milder than the monoamine oxidase inhibitors and the tricyclic antidepressants, SSRIs also produce numerous side effects. For example, SSRIs, including fluoxetine, paroxetine, fluvoxamine, sertraline, and citalopram, are associated with gastrointestinal distress, jitteriness, agitation and sleep disruption.

In addition to the numerous side effects associated with traditional antidepressant medications, these therapeutics are also characterized by marginal efficacy. Several studies on the efficacy of antidepressant therapy for major depression have concluded that the treatment of acute disease or maintenance therapy is associated with a 50-60% response rate. (Schulberg et al. (1998) *Arch. Gen. Psychiatry* 55: 1121). The average absolute response rate between antidepressants and placebo is about 20-25%. (Williams et al. (2000) *Ann. Intern. Med.* 132: 743). Consequently, there is a current need for new antidepressant therapies.

In view of the sometimes severe adverse side effects and marginal efficacy of numerous antidepressant therapies, there is a great need for improved pharmaceuticals that effectively treat depressive disorders without producing the side effects associated with treatments of depression. The present invention identifies those compounds that enhance or improve learning and memory as a new class of therapeutics for the treatment of depressive disorders.

B. Carbonic Anhydrase

Carbonic anhydrase, a zinc-containing enzyme that catalyzes the interconversion of carbon dioxide and bicarbonate anion, is present throughout the body, including the brain. (Sun et al. (2002) *Trends in Pharm. Sci.* 23(2): 83-89; incorporated herein by reference in its entirety). Carbonic anhydrase II, the most active of the seven human isozymes, is a 23.9 kDa enzyme found primarily in erythrocytes, glial cells and brain neurons. (Id). In addition to its involvement in pH regulation, bicarbonate reabsorption and carbon dioxide expiration, carbonic anhydrase plays a crucial role in signal processing, long-term synaptic transformation and attentional gating of memory storage. (Id.).

Carbonic anhydrase dysfunction has been associated with mental retardation, Alzheimer's disease, and impaired cognition. Conversely, the activation of carbonic anhydrase has been demonstrated to improve learning and memory. (Id.; U.S. Patent Application Serial Nos. PCT/US02/13784; PCT/US03/07102; 60/287,721; 60/362,081; Ser. Nos. 10/172,005; and 10/476,459; each incorporated herein by reference in its entirety). Prior to the present disclosure, however, the carbonic-anhydrase-mediated improvement of learning and memory has not been recognized as a mechanism for the treatment of depressive disorders. Although a recent biochemical study using isolated carbonic anhydrase identified three SSRIs, fluoxetine, sertraline and citalopram, as activators of carbonic anhydrase, these experiments did not demonstrate that carbonic anhydrase activation is the mechanism whereby the symptoms of depressive disorders are ameliorated. (Casini et al. (2003) *Bioorg. Med. Chem. Lett.* 13: 2765-2768).

Carbonic anhydrase activity is regulated by signaling pathways that include ryanodine receptor-mediated signaling pathways. The intracellular release of calcium through ryanodine receptors, for example, is involved in the GABA-mediated synaptic switch. (Sun et al. (2002) *Trends in Pharmacol. Sci.* 23(2): 83-89). Activation of ryanodine receptors in CA1 pyramidal cells, combined with depolarization induced calcium loading, transforms GABA-mediated responses, an effect that is blocked by ryanodine-receptor antagonists or carbonic anhydrase inhibitors. (Sun et al. (2000) *Proc. Nat'l Acad Sci USA* 97: 12300-12305). The effect of calcium on carbonic anhydrase, however, appears to be indirect. For example, early studies show that calcium potentiates the activation of either purified carbonic anhydrase or gastric mucosa carbonic anhydrase by histamine and other agents. (Puscas et al. (1996) *J. Pharmacol. Exp. Ther.* 277: 1464-1466). In addition, the dose-dependent inhibition of carbonic anhydrase by verapamil also implicates calcium in the activation of carbonic anhydrase. Furthermore, in human myelomonocytic cell lines, the synthesis of carbonic anhydrase II is activated by protein kinase C. (Sun et al. (2002) *Trends in Pharmacol. Sci.* 23(2): 83-89). Consequently, the PKC-mediated increase in carbonic anhydrase synthesis can increase carbonic anhydrase activity that has a resultant antidepressant effect.

C. Protein Kinase C

PKC has been identified as one of the largest gene families of non-receptor serine-threonine protein kinases. Since the discovery of PKC in the early eighties by Nishizuka and coworkers (Kikkawa et al. (1982) *J. Biol. Chem.* 257: 13341), and its identification as a major receptor for phorbol esters (Ashendel et al. (1983) *Cancer Res.*, 43: 4333), a multitude of physiological signaling mechanisms have been ascribed to this enzyme. The intense interest in PKC stems from its unique ability to be activated in vitro by calcium and diacylglycerol (and its phorbol ester mimetics), an effector whose formation is coupled to phospholipid turnover by the action of growth and differentiation factors.

The activation of PKC has been shown to improve learning and memory. (U.S. Patent Application Serial Nos. PCT/US02/13784; PCT/US03/07102; 60/287,721; 60/362,081; Ser. Nos. 10/172,005; and 10/476,459; each incorporated herein by reference in its entirety). Prior to the present disclosure, however, the PKC-mediated improvement of learning and memory has not been recognized as a mechanism for the treatment of depressive disorders. Also, the PKC activators disclosed herein, specifically those compounds that improve learning and memory, were not recognized as possessing antidepressant activity.

D. Fibroblast Growth Factor-18 (FGF-18)

Fibroblast Growth Factor-18 (FGF-18) has been shown to improve learning and memory. (U.S. Provisional Application Ser. No. 60/429,321 and PCT/IB03/05408, which are both incorporated by reference herein in their entireties). Binding of FGF-18 to its cognate receptor activates a PKC-mediated signaling pathway that implicates both PKC and carbonic anhydrase. Prior to the present disclosure, however, the FGF-18-mediated improvement of learning and memory has not been recognized as a mechanism for the treatment of depressive disorders. Also, FGF-18 has not been recognized as possessing antidepressant activity.

SUMMARY OF THE INVENTION

The present invention provides a new class of therapeutics, compounds and compositions that enhance or improve learning and memory, for the treatment of depressive disorders. The present invention provides methods of treating depressive disorders comprising the administration of compositions comprising compounds that enhance or improve learning and memory.

The present invention provides a method comprising the steps of a) identifying a subject with a depressive disorder; and b) administering an effective amount of a composition comprising a carbonic anhydrase activator and a pharmaceutically acceptable carrier to said subject, wherein the carbonic anhydrase activator being selected from the group consisting of:

(1) Structure I

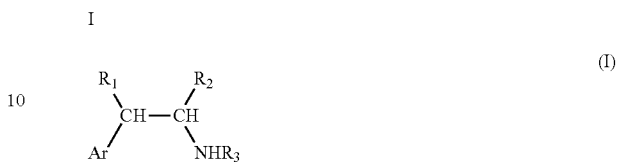

wherein $R_1$ is H or OH; $R_2$ and $R_3$ are independent H, COOH or lower alkyl, for example linear, branched or cyclic $C_1$-$C_6$ alkyl or $C_1$-$C_4$ alkyl; and Ar is phenyl, imidizolyl or phenyl or imidizolyl substituted with one or more halo, hydroxy, amino or lower alkyl groups for example linear, branched or cyclic $C_1$-$C_6$ group or $C_1$-$C_4$ alkyl group;

(2) Structure II:

wherein R1 and $R_2$ are independently H or lower alkyl, for example linear, branched or cyclic $C_1$-$C_6$ alkyl or $C_1$-$C_4$ alkyl;

(3) Structure III:

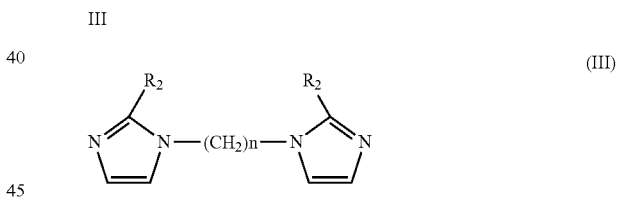

wherein n is 1 or 2 and $R_2$ is H or lower alkyl, for example linear, branched or cyclic $C_1$-$C_6$ alkyl or $C_1$-$C_4$ alkyl; and pharmaceutically acceptable salts of I, II, or III. In one embodiment of the present invention, the activator has structure I, wherein $R_1$ is H or OH; $R_2$ is H, $CH_3$ or COOH; $R_3$ is H or $CH_3$; and Ar is phenyl, or a substituted phenyl. In a preferred embodiment, the substituted phenyl is 4-hydroxyphenyl, 4-fluorophenyl, 4-aminophenyl, 3-amino-4-hydroxyphenyl, or 3,4-dihydroxyphenyl.

The present invention also contemplates methods using derivatives and analogs of the carbonic anhydrase activators disclosed herein, wherein the derivatives and analogs increase the potency of the carbonic anhydrase activating effect, increase the specificity to carbonic anhydrase as compared to other targets, reduce toxicity, improve stability in an oral dosage form, and/or enhance the ability of the compound to cross the blood brain barrier (pro-drugs). Derivatives are compounds formed by adding or removing side chains from the listed compounds. Analogs are structural variants of the compounds having enhanced similar physical and/or chemical properties with respect to the binding site of carbonic anhydrase. Derivates and analogs according to the invention are those which are able to deliver the activator compounds of the invention to the brain of a subject.

In one embodiment of the present invention, the carbonic anhydrase activators provide neuronal carbonic anhydrase activity of at least about 110, 115, 125, 135, 150, 170, 180, 190, 200, 210, 220, 220, 230, 240 and 250% that of alanine.

In one embodiment, the activator of the present invention is an aromatic amine or an aromatic amino acid of structure I, II or III. In a preferred embodiment, the activator activates intraneuronal carbonic anhydrase. In another embodiment, the activator activates carbonic anhydrase II between 1.5- and 2-times more than alanine, in vitro.

In another embodiment of the present invention, the activator has structure I wherein $R_1$ is H or OH; $R_2$ is H, $CH_3$ or COOH; $R_3$ is H or $CH_3$; and Ar is imidazole or a substituted imidazole. In a preferred embodiment, the substituted imidazole is imadazol-4-yl-, or 5-methylimidazole-4-yl-.

In a preferred embodiment, the activator is selected from the group consisting of: imidazole, phenylalanine, a substituted ethylamine, phenethylamine, histamine, histidine, a linked di-imidazole, a triazole, and pharmaceutically acceptable salts thereof. More preferably the activator is histidine; histamine; phenylalanine; 4-hydroxy phenylalanine; 4-fluoro phenylalanine; 3,4-dihydroxy phenylalanine; 3-amino-4-hydroxyphenylalanine; 4-amino phenylalanine; tyrosine; dopamine; noradrenaline; adrenaline or 5-methyl histamine.

The present invention also provides a method comprising the steps of a) identifying a subject with a depressive disorder; and b) administering an effective amount of a composition comprising a carbonic anhydrase activator and a pharmaceutically acceptable carrier to said subject, wherein the activator has structure II and further wherein $R_1$ is H, methyl, ethyl or propyl; and $R_2$ is H or methyl. In one embodiment, the activator activates carbonic anhydrase II between 1.5- and 2-times more than alanine, in vitro.

The present invention also provides a method comprising the steps of a) identifying a subject with a depressive disorder; and b) administering an effective amount of a composition comprising a carbonic anhydrase activator and a pharmaceutically acceptable carrier to said subject, wherein the activator is structure III and further wherein n is 1 or 2; and $R^2$ is H or methyl. In one embodiment, the activator activates carbonic anhydrase II between 1.5- and 2-times more than alanine, in vitro.

The present invention also provides methods of treating depression in a subject in need thereof, comprising administering an effective amount of a composition comprising a carbonic anhydrase activator and a pharmaceutically acceptable carrier, wherein the activator is selected from the group consisting of: an aromatic amine or an aromatic amino acid, wherein the aromatic amine or aromatic amino acid contains a single aromatic group. In one embodiment, the aromatic amine or aromatic amino acid activates carbonic anhydrase II between 1.5- and 2-times more than alanine. In a preferred embodiment, the activator is an aromatic amino acid selected from the group consisting of: phenylalanine, a substituted phenylalanine, histidine, a substituted histidine, a substituted phenylalanineimidazole, a substituted imidazole, a linked di-imidazole, and a linked substituted di-imidazole. Preferably, the activator is an aromatic amine selected from the group consisting of dopamine, noradrenaline, adrenaline, histamine, and 5-methyl histamine.

The present invention provides a method comprising the steps of a) identifying a subject with a depressive disorder and b) administering an effective amount of a composition comprising a protein kinase C activator and a pharmaceutically acceptable carrier to said subject, wherein the PKC activator is selected from a group consisting of: FGF-18, a macrocyclic lactone, a benzolactam, a pyrrolidinone, or a combination thereof. In a preferred embodiment, the macrocyclic lactone is a bryostatin or neristatin. In a more preferred embodiment, the bryostatin is selected from a group consisting of bryostatin-1, 2, 3, 4, 5, 6, 7, 8, 9, 10, 11, 12, 13, 14, 15, 16, 17 and 18. Most preferably, the bryostatin is bryostatin-1 and the neristatin is neristatin-1.

The present invention also provides methods of treating depression in a subject in need thereof, comprising administering an effective amount of a composition comprising a protein kinase C activator and a pharmaceutically acceptable carrier, wherein the activator is selected from the group consisting of: FGF-18, a macrocyclic lactone, a benzolactam, a pyrrolidinone, or a combination thereof. In a preferred embodiment, the macrocyclic lactone is a bryostatin or neristatin. In a more preferred embodiment, the bryostatin is selected from a group consisting of bryostatin-1, 2, 3, 4, 5, 6, 7, 8, 9, 10, 11, 12, 13, 14, 15, 16, 17 and 18. Most preferably, the bryostatin is bryostatin-1 and the neristatin is neristatin-1.

The present invention also provides methods of treating depression in a subject in need thereof, comprising administering an effective amount of a composition comprising one or more of the following: tacrine (marketed under the tradename COGNEX®), velnacrine, donepezil (marketed under the tradename ARICEPT®), galantamine (marketed under the tradename REMINYL®), memantine (marketed under the tradename NAMENDA®), or pharmaceutically acceptable salts thereof.

The present invention also provides methods for screening an agent for antidepressant activity, comprising the steps of:

a) administering an agent in a pharmaceutically acceptable carrier to a test subject and administering the pharmaceutically acceptable carrier to the control subject;

b) individually placing said test and control subject into a pool of water and measuring the distance and/or duration of swimming during a testing period; and c) comparing the distance or duration of swimming of the test subject to a control subject, wherein increased distance or duration of swimming of the test subject compared to the control subject is indicative of antidepressant activity.

In a preferred embodiment, the water pool is round. Preferably, the pool has a diameter of between 100 and 200 cm. More preferably, the pool has a diameter of 150 cm. Preferably, the pool provides no escape.

In another embodiment, steps (a), (b), and (c) are repeated. Preferably, the steps are repeated three times.

In the methods for screening an agent for antidepressant activity of the present invention, the distance and/or duration of swimming is preferably measured by video means.

DETAILED DESCRIPTION OF THE INVENTION

A. Definitions

Figure 1:
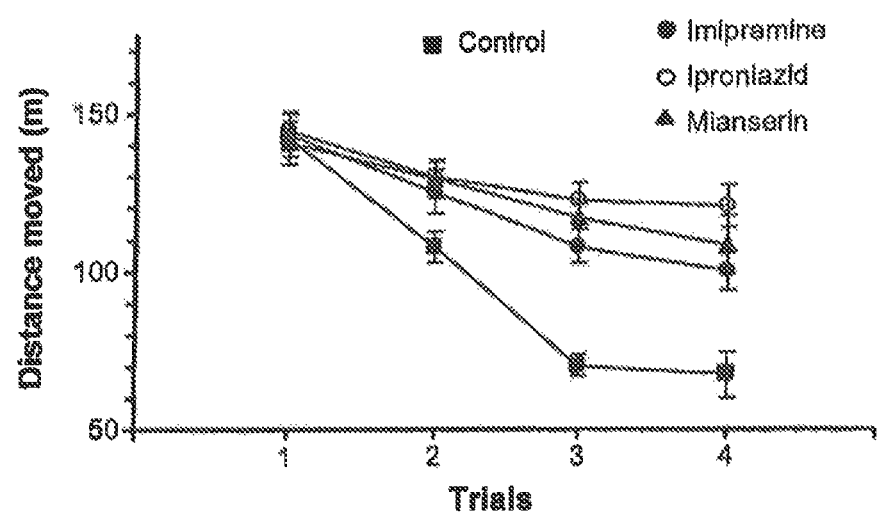
FIG. 1 depicts the effect of three antidepressants, imipramine, iproniazid and mianserin, on the mobility of rats in the open-space-swimming test.

As used herein, "administration" of a composition includes any route of administration, including oral subcutaneous, intraperitoneal, and intramuscular.

As used herein, the term "aromatic" means a cyclically conjugated molecular entity with a stability significantly greater than that of a hypothetical localized structure. As used herein, aromatic compounds include polycyclic and heterocyclic compounds.

As used herein, "carbonic anhydrase activator" means a substance that increases the rate of the reaction catalyzed by carbonic anhydrase by binding to the carbonic anhydrase at or near a zinc-bound water.

As used herein, "depressive disorder" means major depression, dysthymia, and atypical depression or depression not otherwise specified.

As used herein, "an effective amount" is an amount sufficient to reduce one or more symptoms associated with a depressive disorder.

As used herein, "protein kinase C activator" or "PKC activator" means a substance that increases the rate of the reaction catalyzed by protein kinase C by binding to the protein kinase C.

As used herein, the term "a single aromatic group" means only one monocyclic or one polycyclic aromatic group.

As used herein, the term "subject" means a mammal.

As used herein, the term "substituted imidazole" means an imidazole moiety with one or more substituent groups attached to the imidazole ring.

As used herein, the term "substituted phenyl" means a phenyl moiety with one or more substituent groups attached to the phenyl ring.

As used herein, the term "pharmaceutically acceptable carrier" means a chemical composition with which the active ingredient may be combined and which, following the combination, can be used to administer the active ingredient to a subject. As used herein, the term "physiologically acceptable" ester or salt means an ester or salt form of the active ingredient which is compatible with any other ingredients of the pharmaceutical composition, which is not deleterious to the subject to which the composition is to be administered.

As used herein, "pharmaceutically acceptable carrier" also includes, but is not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents; demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and other mammals.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. In addition to the active ingredient, a pharmaceutical composition of the invention may further comprise one or more additional pharmaceutically active agents. Particularly contemplated additional agents include anti-emetics and scavengers such as cyanide and cyanate scavengers. Controlled- or sustained-release formulations of a pharmaceutical composition of the invention may be made using conventional technology.

The effective dose for administration of the compounds is one that enhances carbonic anhydrase activity in cells of neuronal signaling pathways. Typically dosages of the compound of the invention which may be administered to an animal, preferably a human, range in amount from 1 mg to about 100 grams check the invention disclosure per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal. Most preferably, the dosage is between 50 and 100 mg per kilogram of body weight of the animal and is administered orally three times daily.

Extrapolating from rat dosing, which predictive of human dosing, effective does of a phenylalanine (50 mM) or imidazole (0.5 M) agents for treating humans may include the equivalent of 0.1, 0.3, 1, 3 or 10 ml/kg body weight taken thrice daily.

The invention encompasses derivatives and analogs of these compounds which increase the potency of the carbonic anhydrase activating effect, increase the specificity to carbonic anhydrase as compared to other targets, reduce toxicity, improve stability in an oral dosage form, and/or enhance the ability of the compound to cross the blood brain barrier (pro-drugs). Derivatives are compounds formed by adding or removing side chains from the listed compounds. Analogs are structural variants of the compounds having enhanced similar physical and/or chemical properties with respect to the binding site of carbonic anhydrase. Derivates and analogs according to the invention are those which are able to deliver the activator compounds of the invention to the brain of a subject.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the memory, attention or learning deficit being treated, the type and age of the animal, etc.

B. Depressive Disorders

Depressive disorders encompass the diagnoses of major depression, dysthymia, and atypical depression or depression not otherwise specified ("minor depression"). The different subgroups of depressive disorders are categorized and defined by the Diagnostic and Statistical Manual of Mental Disorders, Fourth Edition (DSM-IV). (American Psychiatric Association. Diagnostic and Statistical Manual of Mental Disorders, $4^{th}$ Ed., Primary Care Version (DSM-IV-PC). American Psychiatric Association Press, Washington, D.C. 1995). According to the DSM-IV, a diagnosis of "major depression" requires that a patient present with at least five of the following nine symptoms during the diagnostic period: 1) depressed mood most of the day (most acute in the morning); 2) markedly diminished interest or pleasure in nearly all activities (anhedonia); 3) significant weight loss or gain; 4) insomnia or hypersomnia; 5) psychomotor agitation or retardation; 6) fatigue or energy loss; 7) feelings of guilt and worthlessness; 8) impaired concentration and indecisiveness; and 9) recurring thoughts of death or suicide. To support a diagnosis of major depression, a depressed mood or loss of interest (anhedonia) must be one of the five observed symptoms. In contrast, a diagnosis of "atypical depression" or "depression not otherwise specified" (also referred to as "minor depression"), the most common form of depression, requires between 2 and 4 depressive symptoms that are present daily or for most of the day for at least a two week period. Dysthymia is a chronic, low intensity mood disorder characterized by anhedonia, low self esteem and low energy that persists for more than two years, consecutively. Seasonal affective disorder is considered to be a form of major depression characterized by seasonal variation.

C. Animal Models

Despite progress toward the development of new therapeutic agents and availability of several animal models, there is still a pressing need for improved animal models for screening antidepressant activity of candidate compounds. (Cryan et al. 2002 *Trends Pharmacol* 23: 238-45). Currently, the most widely used animal models of depression include the forced-swimming tests, tail-suspension test, and olfactory bulbectomy (Cryan et al. (2002) *Trends Pharmacol.* 23: 238-45). The forced-swimming test measures immobility of animals in an inescapable cylinder of water, 24 h after a 15 minute pretest in the same cylinder. It is the most widely-used model for preclinical prediction of antidepressant activity, but requires judgments and scoring by the investigators. The test does not reliably predict the antidepressant activity of selective serotonin-reuptake inhibitors (Porsolt (1990) Behavioral Despair: Present Status and Future Perspectives, In: Antidepressants: Thirty Years On, CNS Publishers 85-94; Porsolt et al. (1991) Pharmacological Models of Depression, In: Animal Models in Psychopharmacology, Advances in Pharmacological Sciences. Basel: Birkhauser 137-59; Takamori et al. (2001) *Pharmacology* 73: 147-53; Cryan et al. (2002) *Trends Pharmacol.* 23: 238-45) and requires a modified scoring to improve detection (Detke et al. (1995) *Psychopharmacology* 121: 66-72; Detke et al. (1996) *Behav. Brain Res.* 73: 43-46; Cryan et al. (2002) *Trends Pharmacol.* 23: 238-245). The tail-suspension test induces a state of a lack of despair characterized by a lack of effort or struggle to escape, that is acutely reversed by antidepressants. Some animals, however climb their tails. Olfactory bulbectomy, bilateral removal of the olfactory bulbs, on the other hand, results in a behavioral change correlated with changes in the depression. A hyperactive response in a novel, brightly lit open field apparatus, is reversed chronically, but not acutely, by antidepressant treatment (Kelly et al. (1997) *Pharmacol. Ther.* 74: 299-316). However, the test is based on the behavioral similarity to depression. Its mechanism of action is poorly understood. For more detailed discussion of a variety of animal models, the reader is referred to two recent review articles (Cryan et al. 2000 *Trends Pharmacol.* 23: 238-245; Nestler et al. (2002) *Neuron* 34: 13-25).

To improve the understanding of the causal mechanisms of depression, we need animal models that mirror the situation in patients (Cryan et al. 2000 *Trends Pharmacol.* 23: 238-245). One difference between human depression and the standard forced swimming model (also called the behavioral-despair model) is that human depression is manifested in a majority of cases as a lack of motivation (hopelessness) and does not have a direct counterpart to the main feature of the forced-swing model—a lack of "physical space" that operates as the inducer of depression.

The present invention provides an improved animal model of depression with increased predictive power. To elucidate whether the open-space-swimming model has "predictive validity", rats were treated with all three major antidepressants. These experiments demonstrated a time-dependent restoration of behavioral parameters as compared with untreated animals. Imipramine, a tricyclic antidepressant (inhibitor of serotonin and norepinephrine reuptake transporters), iproniazid, a monoamine oxidase inhibitor, and mianserin, an atypical antidepressant were used in the study of, for their effectiveness in clinics and representative of each class. It is a common practice to evaluate the suitability of animal models of depression by examining effectiveness of all three prototypical antidepressants. Unlike the forced swimming test, the restricted space would not be a determining factor in the open space swimming test and the mobility is directly measured without an involvement of human judgment and scoring. Our results show that the test has a high predictivity of antidepressant drugs, including an SSRI, and improved sensitivity to antidepressant treatment. The distance moved measures active swimming status of the animals during the trial period. In addition, it is sensitive to SSRIs without any requirement of a scoring modification. It may have value as a choice of depressive models in revealing pathophysiological mechanism(s) of depression and searching for new classes of antidepressants.

Animal models are indispensable in searching for new antidepressants and for clarifying pathophysiology that underlies depression. On the other hand, the availability of clinically active antidepressants has also made it possible to develop and validate a wide range of behavioral tests to study depression-like phenotypes in animal models. In our open space model, rats quickly and reproducibly became immobile, exhibiting increased "floating" inactivity over the course of the trials. The validity of the open-space-swimming test for depression was confirmed by results obtained by testing animals treated with known antidepressants. All three major classes of antidepressants were represented in this study: imipramine, a tricyclic antidepressant (inhibition of serotonin or norepinephrine reuptake transporters); iproniazid, a monoamine oxidase inhibitor; and mianserin, an atypical antidepressant, and alaproclate, an SSRI. The applied dose in our study was similar/identical to those used in rats in antidepressant studies without inducing changes in non-specific locomotor activity (Bai et al. (2001) *Pharmacol. Biochem. Behav.* 70: 187-192; Kroczka et al. (2001) *Brain Res. Bull.* 55: 297-300; Takamori et al. (2001) *Pharmacology* 63: 147-153; Kitamura et al. (2002) *Pharmacol. Biochem. Behav.IY* 63-69).

Results from the open-space-swimming test can be compared with previously reported data (Porsolt et al. (1977) *Nature* 266: 730-730-732; Porsolt et al. (1978) *Eur J. Pharmacol.* 47: 379-391), in which three similar i.p. doses (15 mg/kg) of these traditional antidepressants were applied to the same age of rats in the forced-swimming test. The percentages of decreases in the distance moved on the third day (using the decrease of control groups as 100%) in our study for the imipramine, iproniazid, and mianserin groups were 49.8±7.6% (n=8), 44.0±7.7% (n=8), and 33.3±6.3% (n=8), respectively, compared with immobility % as control of 61.5±6.5% (n=5; 15 mg/kg×3 per day; P<0.01; Porsolt et al. (1977) *Nature* 266: 730-730-732; 87.6±7.3% (n=5, 15 mg/kg×3 per day; P<0.01; Porsolt et al. (1978) *Eur J. Pharmacol.* 47: 379-391), and 66.5±7.0% (n=5, 15 mg/kg×3 per day; P<0.01; Porsolt et al. (1977) *Nature* 266: 730-730-732) in the forced swimming test, respectively. Thus, the rats tested using the open-space-swimming test were more sensitive to the antidepressant treatments with statistically significant differences of the iproniazid ($F_{1,12}$=11.65; P<0.01) as compared with the previously reported data.

The open-space-swimming tests satisfies three of the four minimum requirements (McKinney et al. (1969) *Arch Gen Psychiatr Vol.* 21, 240-8; Cryan et al. (2002) *Trends Pharmacol* 23: 238-45) for an animal model of depression. These requirements for a suitable animal model include (1) reasonably analogous to the human disorder in its manifestations or symptomatology; (2) the existence of a behavioral change that can be monitored objectively; (3) reversibility of the behavioral change by the same treatments that are effective in human; and (4) reproducible between investigators. Reliability across laboratories remains to be tested. The rat forced swimming test, which has been used for many years, is generally viewed as a test with high predictivity of antidepressant efficacy in human depression (Porsolt et al. (1977) *Nature* 266: 730-730-732). Its value in searching for new types of effective drugs is not clear.

The open-space-swimming model has several advantages. First, one obvious advantage of this test over the leading forced swimming test is that, unlike those time-sampling judgment and scoring in the forced swimming test (Kroczka et al. (2001) *Brain Res Bull* 55: 297-300; Reneric et al. (2002) *Eur. Neuropsychopharmacol.* 12: 159-71), no human judging and scoring are involved in this test so that the monitoring is more objective. Second, objective monitoring offers the possibility of improving the reproducibility across different laboratories. Third, the forced-swimming test does not reflect the extent or degree of a behavior, such as vigorous, moderate, or mild swimming mobility. In contrast. These characteristics are directly measured in the open-space-swimming test. In addition, no climbing behavior was observed in the open space model, probably due to the large space available. This removes another artificial judgment as whether climbing should account for more than or equal to active swimming in the forced-swimming test. Fourth, this test does not limit the animals' movement due to space restriction and mimics the human disorder more closely. It is the lack of motivation (opportunities or hope) rather than the restricted "physical space" that largely (though not exclusively) defines the human disease.

D. Carbonic Anhydrase

Carbonic anhydrase, a zinc-containing enzyme that catalyzes the interconversion of carbon dioxide and bicarbonate anion, is present throughout the body, including the brain. (Sun et al. (2002) *Trends in Pharm. Sci.* 23(2): 83-89; incorporated herein by reference in its entirety). Carbonic anhydrase II, the most active of the seven human isozymes, is a 23.9 kDa enzyme found primarily in erythrocytes, glial cells and brain neurons. (Id.). In addition to its involvement in pH regulation, bicarbonate reabsorption and carbon dioxide expiration, carbonic anhydrase plays a crucial role in signal processing, long-term synaptic transformation and attentional gating of memory storage. (Id.). Carbonic anhydrase dysfunction has been associated with mental retardation, Alzheimer's disease, and impaired cognition, and the activation of carbonic anhydrase has been demonstrated to improve memory and learning. (Id; U.S. Patent Application Ser. Nos. PCT/US02/13784; PCT/US02/14378; PCT/US03/07102; 60/287,271; 60/289,137; 60/362,081; Ser. Nos. 10/172,005; 10/476,459; and Ser. No. 10/477,121; each incorporated herein by reference in its entirety).

Carbonic anhydrase catalyzes a reversible reaction between $CO_2$ hydration and $HCO_3^-$ dehydration. Recent studies indicate that activation of this enzyme provides a rapid and efficient mechanism to raise $HCO_3^-$ concentrations in memory-related neural structures. Increased $HCO_3^-$ flux through synaptic $GABA_A$ receptor channels alters postsynaptic neuronal responses to GAB A and thus neuronal responses to diverse signal inputs. In this way, carbonic anhydrase functions as an effective attentional gate that controls signal transfer through the neural network. Alterations in carbonic anhydrase activity in hippocampal CA1 neurons provide a mechanism for switching between operational states at GABA releasing synapses, thereby gating signal transfer through the hippocampal network.

Carbonic anhydrase activity is at least partially activated by intracellular release of $Ca^{2+}$ through the ryanodine receptors (Rye). For example, the RyR is involved in the GABA-mediated synaptic switch. The effect of $Ca^{2+}$ on carbonic anhydrase appears to be indirect. In human myelomonocytic cell lines, synthesis of carbonic anhydrase II is activated by protein kinase C, an effect that is blocked by 0.1 Jim staurosporine. Hormones also regulate the activity of carbonic anhydrase via cAMP. Thus, the increase in carbonic anhydrase activity induced by adrenaline and dibutyryl-cAMP in erythrocytes is enhanced by theophylline, and phosphorylation by a cAMP-dependent protein kinases activates carbonic anhydrase.

There are at least seven isozymes of carbonic anhydrase in humans. (Lindskog (1991) *Pharmacol. Ther.* 74(1): P 1-20). The structure of the CAII binding site for acetazolamide and some other inhibitors is known. This knowledge allows rational design of derivatives and analogs of the compounds contemplated herein.

Based on structural, biochemical and medicinal chemistry studies, the pharmacological profile of carbonic anhydrase has been refined and specific activators have been developed. Activators of carbonic anhydrase provided an important tool for the treatment of genetic carbonic anhydrase deficiencies and memory disorders. Many amines and amino acids (e.g., dopamine, seratonin, noradrenaline, adrenaline, histamine, histidine, imidazoles, phenylalanine or derivatives thereof (See, WO 00/56760, which is incorporated herein by reference in its entirety)) are carbonic anhydrase activators. Specifically, carbonic anhydrase activators increase the rate of interconversion of carbon dioxide and bicarbonate ion (Reaction I) by acting directly as proton acceptors.

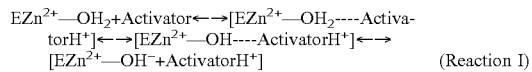
(Reaction I)

Carbonic anhydrase activators encompassed by the present invention and the activation by each of human carbonic anhydrase II activity (relative to the activation of the enzyme by alanine) is depicted in Table I.

TABLE 1

Carbonic Anhydrase Activators

| Effector | Ar | R1 | R2 | R3 | % Activity/ Control CAII Activity |
|---|---|---|---|---|---|
| 1 | H | H | COOH | H | 100 |
| 2 | Phenyl | H | COOH | H | 186.7 |
| 3 | Phenyl | H | H | H | 109.5 |
| 4 | 4-Hydroxyphenyl | H | COOH | H | 189.1 |
| 5 | 4-Fluorophenyl | H | COOH | H | 167.7 |
| 6 | 4-Aminophenyl | H | COOH | H | 159.4 |
| 7 | 3-Amino-4-hydroxyphenyl | H | COOH | H | 176.3 |
| 8 | 3,4-Dihydroxyphenyl | H | COOH | H | 134.3 |
| 9 | 3,4-Dihydroxyphenyl | H | H | H | 137.5 |
| 10 | 3,4-Dihydroxyphenyl | OH | H | H | 115.5 |
| 11 | 3,4-Dihydroxyphenyl | OH | H | $CH_3$ | 135.0 |
| 12 | 3,4-Dihydroxyphenyl | OH | $CH_3$ | H | 129.0 |
| 13 | Phenyl | OH | $CH_3$ | $CH_3$ | 134.5 |
| 14 | Imidazole | (Ar only, no rest C—C chain) | | | 230.0 |
| 15 | Imadazol-4-yl | H | H | H | 150.0 |
| 16 | Imadazol-4-yl | H | COOH | H | 170.0 |
| 17 | 5-Methylimidazole-4-yl | H | H | H | 130.5 |

E. Protein Kinase C (PKC)

The PKC gene family consists presently of 11 genes which are divided into four subgroups: 1) classical PKCα, $\beta_1$, $\beta_2$ ($\beta_1$ and $\beta_2$ are alternatively spliced forms of the same gene) and γ, 2) novel PKCδ, ε, η, and θ, 3) atypical PKCζ, λ, η and ί and 4) PKC μ PKC μ resembles the novel PKC isoforms but differs by having a putative transmembrane domain (reviewed by Blohe et al. (1994) *Cancer Metast. Rev.* 13: 411; Ilug et al. (1993) *Biochem J.* 291: 329; Kikkawa et al. (1989) *Ann. Rev. Biochem.* 58: 31). The α, $\beta_1$, $\beta_2$ and γ isoforms are $C^{2+}$, phospholipid and diacylglycerol-dependent and represent the classical isoforms of PKC, whereas the other isoforms are activated by phospholipid and diacylglycerol but are not dependent on $Ca^{2+}$. All isoforms encompass 5 variable (V1-V5) regions, and the α, β and γ isoforms contain four (C1-C4) structural domains which are highly conserved. All isoforms except PKC α, β and γ lack the C2 domain, the λ and isoforms also lack nine of two cysteine-rich zinc finger domains in CI to which diacylglycerol binds. The CI domain also contains the pseudosubstrate sequence which is highly conserved among all isoforms, and which serves an autoregulartory function by blocking the substrate-binding site to produce an inactive conformation of the enzyme (House et al. (1987) *Science* 238, 1726).

Because of these structural features, diverse PKC isoforms are thought to have highly specialized roles in signal transduction in response to physiological stimuli (Nishizuka (1989) *Cancer* 10: 1892), as well as in neoplastic transformation and differentiation (Glazer (1994) *Protein Kinase C*, J. F. Kuo, ed., Oxford U. Press at pages 171-198). For a discussion of known PKC modulators see PCT/US97/ 08141, U.S. Pat. Nos. 5,652,232; 6,080,784; 5,891,906; 5,962,498; 5,955,501; 5,891,870 and 5,962,504 (each incorporated herein by reference in its entirety).

The anti-depressant effect of PKC activators is mediated directly by activation of PKC and/or the increased synthesis of carbonic anhydrase observed following PKC activation.

There is increasing evidence that the individual PKC isozymes play different, sometimes opposing, roles in biological processes, providing two directions for pharmacological exploitation. One is the design of specific (preferably, isozyme specific) inhibitors of PKC. This approach is complicated by the act that the catalytic domain is not the domain primarily responsible for the isotype specificity of PKC. The other approach is to develop isozyme-selective, regulatory site-directed PKC activators. These may provide a way to override the effect of other signal transduction pathways with opposite biological effects. Alternatively, by inducing down-regulation of PKC after acute activation, PKC activators. These may provide a way to override the effect of other signal transduction pathways with opposite biological effects. Alternatively, by inducing down-regulation of PKC after acute activation, PKC activators may cause long term antagonism. Bryostatin is currently in clinical trials as an anti-cancer agent. The bryostatins are know to bind to the regulatory domain of PKC and to activate the enzyme. Bryostatins an example of isozyme-selective activators of PKC. Compounds in addition to bryostatins have been found to modulate PKC. (see for example WO 97/43268; incorporated herein by reference in its entirety). For a discussion of known PKC modulators see PCT/US97/08141, U.S. Pat. Nos. 5,652,232; 6,043,270; 6,080,784; 5,891,906; 5,962,498; 5,955,501; 5,891,870 and 5,962,504 (each of which is incorporated herein by reference in its entirety).

Several classes of PKC activators have been identified. Phorbol esters, however, are not suitable compounds for eventual drug development because of their tumor promotion activity, (Ibarreta et al. (1999) *Neuro Report* 10(5&6): 1035-40). Of particular interest are macrocyclic lactones (i.e. bryostatin class and neristatin class) that act to stimulate PKC. Of the bryostatin class compounds, bryostatin-1 has been shown to activate PKC and proven to be devoid of tumor promotion activity. Bryostatin-1, as a PKC activator, is also particularly useful since the dose response curve of bryostatin-1 is biphasic. Additionally, bryostatin-1 demonstrates differential regulation of PKC isozymes, including PKC☐, PKC☐ and PKC☐. Bryostatin-1 has undergone toxicity and safety studies in animals and humans and is actively investigated as an anti-cancer agent. Bryostatin-1's use in the studies has determined that the main adverse reaction in humans is myalgia. One example of an effective dose is 20 or 30 ug/kg per dose by intraperitoneal injection.

Macrocyclic lactones, and particularly bryostatin-1, are described in U.S. Pat. No. 4,560,774 (incorporated herein by reference in its entirety). Macrocyclic lactones and their derivatives are described elsewhere in U.S. Pat. No. 6,187, 568, U.S. Pat. No. 6,043,270, U.S. Pat. No. 5,393,897, U.S. Pat. No. 5,072,004, U.S. Pat. No. 5,196,447, U.S. Pat. No. 4,833,257, and U.S. Pat. No. 4,611,066 (each incorporated herein by reference in its entirety). The above patents describe various compounds and various uses for macrocyclic lactones including their use as an anti-inflammatory or anti-tumor agent. (Szallasi et al. (1994) *Journal of Biological Chemistry* 269(3): 2118-24; Zhang et al. (1996) *Cancer Research* 56: 802-808; Hennings et al. (1987) *Carcinogenesis* 8(9): 1343-1346; Varterasian et al. (2000) *Clinical Cancer Research* 6: 825-828; Mutter et al. (2000) *Bioorganic & Medicinal Chemistry* 8: 1841-1860) (each incorporated herein by reference in its entirety).

As will also be appreciated by one of ordinary skill in the art, macrocyclic lactone compounds and their derivatives, particularly the bryostatin class, are amenable to combinatorial synthetic techniques and thus libraries of the compounds can be generated to optimize pharmacological parameters, including, but not limited to efficacy and safety of the compositions. Additionally, these libraries can be assayed to determine those members that preferably modulate a-secretase and/or PKC.

Combinatorial libraries high throughput screening of natural products and fermentation broths has resulted in the discovery of several new drugs. At present, generation and screening of chemical diversity is being utilized extensively as a major technique for the discovery of lead compounds, and this is certainly a major fundamental advance in the area of drug discovery. Additionally, even after a "lead" compound has been identified, combinatorial techniques provide for a valuable tool for the optimization of desired biological activity. As will be appreciated, the subject reaction readily lend themselves to the creation of combinatorial libraries of compounds for the screening of pharmaceutical, or other biological or medically-related activity or material-related qualities. A combinatorial library for the purposes of the present invention is a mixture of chemically related compounds, which may be screened together for a desired property; said libraries may be in solution or covalently linked to a solid support. The preparation of many related compounds in a single reaction greatly reduces and simplifies the number of screening processes that need to be carried out. Screening for the appropriate biological property may be done by conventional methods. Thus, the present invention also provides methods for determining the ability of one or more inventive compounds to bind to effectively modulate a-secretase and/or PKC.

A variety of techniques are available in the art for generating combinatorial libraries described below, but it will be understood that the present invention is not intended to be limited by the foregoing examples and descriptions. (See, for example, Blondelle et al. (1995) *Trends Anal. Chem.* 14: 83; U.S. Pat. Nos. 5,359,115; 5,362,899; U.S. Pat. No. 5,288,514: PCT publication WO 94/08051; Chen et al. (1994) *JACCS* 1 6:266 1: Kerr et al. (1993) *JACCS I* 1 5:252; PCT publications WO92/10092, WO93/09668; WO91/07087; and WO93/20242; each of which is incorporated herein by reference). Accordingly, a variety of libraries on the order of about 16 to 1,000,000 or more diversomers can be synthesized and screened for a particular activity or property.

Analogs of bryostatin, commonly referred to as bryologs, are one particular class of PKC activators that are suitable for use in the methods of the present invention. The following Table summarizes structural characteristics of several bryologs, demonstrating that bryologs vary greatly in their affinity for PKC (from 0.25 nM to 10 μM). Structurally, they are all similar. While bryostatin-1 has two pyran rings and one 6-membered cyclic acetal, in most bryologs one of the pyrans of bryostatin-1 is replaced with a second 6-membered acetal ring. This modification reduces the stability of bryologs, relative to bryostatin-1, for example, in both strong acid or base, but has little significance at physiological pH. Bryologs also have a lower molecular weight (ranging from about 600 to 755), as compared to bryostatin-1 (988), a property which facilitates transport across the blood-brain barrier.

| Name | PKC Affin (nM) | MW | Description |
| --- | --- | --- | --- |
| Bryostatin 1 | 1.35 | 988 | 2 pyran + 1 cyclic acetal + macrocycle |
| Analog 1 | 0.25 | 737 | 1 pyran + 2 cyclic acetal + macrocycle |
| Analog 2 | 6.50 | 723 | 1 pyran + 2 cyclic acetal + macrocycle |
| Analog 7a | — | 642 | 1 pyran + 2 cyclic acetals + macrocycle |
| Analog 7b | 297 | 711 | 1 pyran + 2 cyclic acetals + macrocycle |
| Analog 7c | 3.4 | 726 | 1 pyran + 2 cyclic acetals + macrocycle |
| Analog 7d | 10000 | 745 | 1 pyran + 2 cyclic acetals + macrocycle, acetylated |
| Analog 8 | 8.3 | 754 | 2 cyclic acetals + macrocycle |
| Analog 9 | 10000 | 599 | 2 cyclic acetals |

Analog 1 (Wender et al. (2004) *Curr Drug Discov Technol.* 1:1; Wender et al. (1998) *Proc Natl Acad Sci USA* 95: 6624; Wender et al. (2002) *Am Chem Soc.* 124: 13648 (each incorporated herein by reference in their entireties)) possesses the highest affinity for PKC. This bryolog is about 100 times more potent than bryostatin-1. Only Analog 1 exhibits a higher affinity for PKC than bryostatin. Analog 2, which lacks the A ring of bryostatin-1 is the simplest analog that maintains high affinity for PKC. In addition to the active bryologs, Analog 7d, which is acetylated at position 26, has virtually no affinity for PKC.

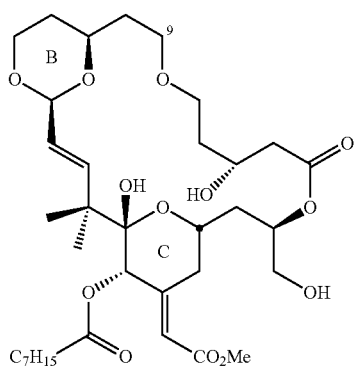

Analog 2; $K_i$ = 8.0 nM

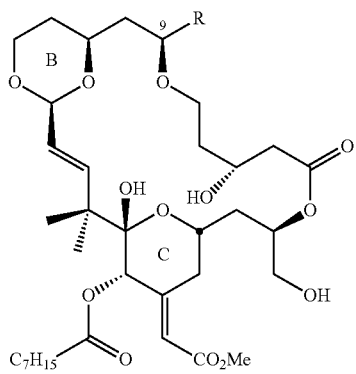

3 R = t-Bu
4 R = Ph
5 R = (CH$_2$)$_3$p-Br—Ph

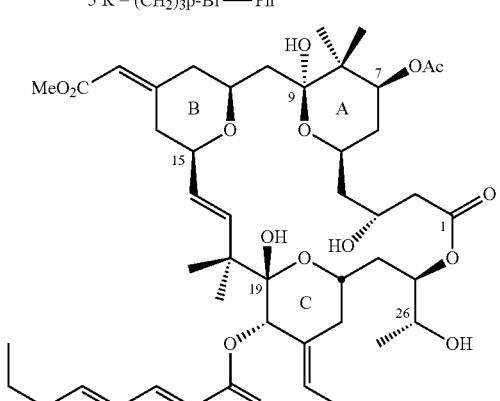

Bryostatin 1; $K_i$ = 1.35 nM

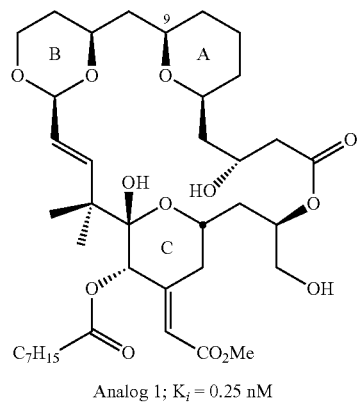

Analog 1; $K_i$ = 0.25 nM

B-ring bryologs are also suitable for use in the methods of the present invention. These synthetic bryologs have affinities in the low nanomolar range (Wender et al. (2006) *Org Lett.* 8: 5299 (incorporated herein by reference in its entirety)). The B-ring bryologs have the advantage of being completely synthetic, and do not require purification from a natural source.

3:

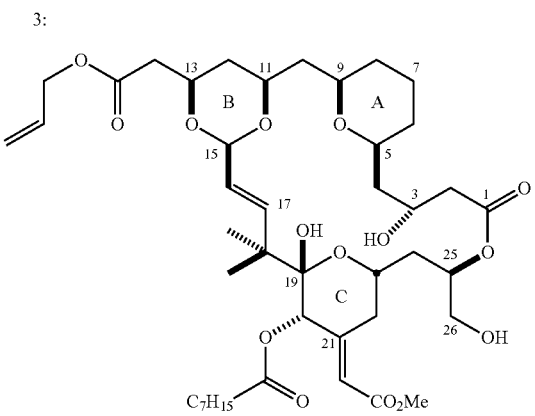

PKC $K_i$ = 1.2 ± 0.6 nM

4:

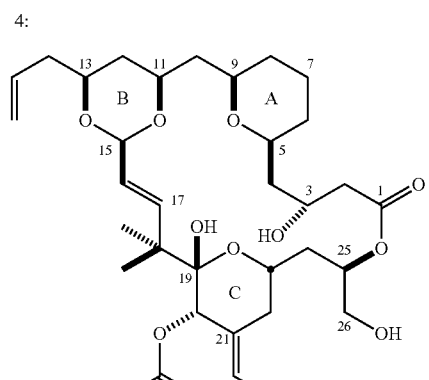

PKC $K_i$ = 0.67 ± 0.5 nM

5:

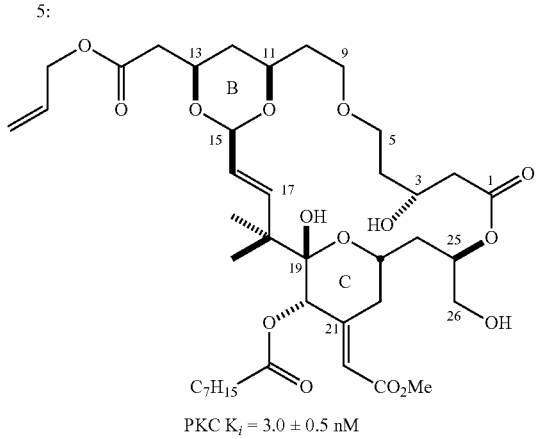

PKC K$_i$ = 3.0 ± 0.5 nM

6:

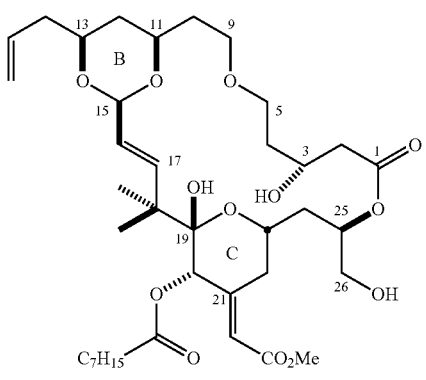

PKC K$_i$ = 2.6 ± 0.5 nM

PKC binding affinities for B-ring bryologs

A third class of suitable bryostatin analogs is the A-ring bryologs. These bryologs have slightly lower affinity for PKC than bryostatin I (6.5, 2.3, and 1.9 nM for bryologs 3, 4, and 5, respectively) but have a lower molecular weight.

A number of derivatives of diacylglycerol (DAG) bind to and activate protein kinase C (Niedel et al. (1983) Proc. Natl. Acad. Sci. USA 80: 36; Mori et al. (1982) J. Biochem (Tokyo) 91: 427; Kaibuchi et al. (1983) J. Biol. Chem. 258: 6701). However, DAG and DAG derivatives are of limited value as drugs. Activation of PKC by diacylglycerols is transient, because they are rapidly metabolized by diacylglycerol kinase and lipase (Bishop et al. (1986) J. Biol. Chem. 261: 6993; Chung et al. (1993) Am. J. Physiol. 265: C927; incorporated herein by reference in their entireties). The fatty acid substitution determines the strength of activation. Diacylglycerols having an unsaturated fatty acid are most active. The stereoisomeric configuration is also critical. Fatty acids with a 1,2-sn configuration are active, while 2,3-sn-diacylglycerols and 1,3-diacylglycerols do not bind to PKC. Cis-unsaturated fatty acids are synergistic with diacylglycerols. In one embodiment of the present invention, the term "PKC activator" expressly excludes DAG or DAG derivatives, such as phorbol esters.

Isoprenoids are PKC activators suitable for use in the methods of the present invention. Farnesyl thiotriazole, for example, is a synthetic isoprenoid that activates PKC with a Kd of 2.5 uM. Farnesyl thiotriazole, for example, is equipotent with dioleoylglycerol (Gilbert et al. (1995) Biochemistry 34: 3916; incorporated herein by reference in its entirety), but does not possess hydrolyzable esters of fatty acids. Farnesyl thiotriazole and related compounds represent a stable, persistent PKC activator. Because of its low MW (305.5) and absence of charged groups, farnesyl thiotriazole would readily cross the blood-brain barrier.

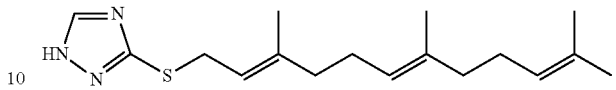

Octylindolactam V is a non-phorbol protein kinase C activator related to teleocidin. The advantages of octylindolactam V, specifically the (−)-enantiomer, include greater metabolic stability, high potency (Fujiki et al. (1987) Adv. Cancer Res. 49: 223; Collins et al. (1982) Biochem. Biophys. Res. Commun. 104: 1159; each incorporated herein by reference in its entirety) (EC$_{50}$=29 nM) and low molecular weight that facilitates transport across the blood brain barrier.

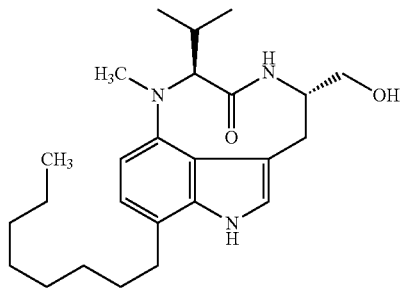 [SMILES: CCCCCCCCc1ccc2c3c(c[nH]c13)C[C@@H](CO)NC(=O)[C@H](C(C)C)N2C]

Gnidimacrin is a daphnane-type diterpene that displays potent antitumor activity at concentrations of 0.1-1 nM against murine leukemias and solid tumors. It acts as a PKC activator at a concentration of ≈3 nM in K562 cells, and regulates cell cycle progression at the G1/S phase through the suppression of Cdc25A and subsequent inhibition of cyclin dependent kinase 2 (Cdk2) (100% inhibition achieved at 5 ng/ml). Gnidimacrin is a heterocyclic natural product similar to bryostatin, but somewhat smaller (MW=774.9).

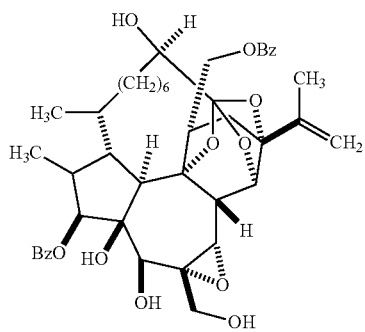

Iripallidal is a bicyclic triterpenoid isolated from Iris pallida. Iripallidal displays anti-proliferative activity in a NCI 60 cell line screen with GI50 (concentration required to inhibit growth by 50%) values from micromolar to nanomolar range. It binds to PKCα with high affinity (Ki=75.6 nM). It induces phosphorylation of ERK1/2 in a RasGRP3-dependent manner. M.W. 486.7. Iripallidal is only about half the size of bryostatin and lacks charged groups.

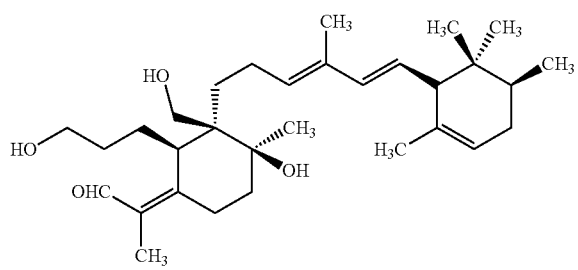

Ingenol [43] is a diterpenoid related to phorbol but possesses much less toxicity. It is derived from the milkweed plant *Euphorbia peplus*. Ingenol 3,20-dibenzoate, for example, competes with [3H]phorbol dibutyrate for binding to PKC (Ki for binding=240 nM) (Winkler et al. (1995) J. Org. Chem. 60: 1381; incorporated herein by reference). Ingenol-3-angelate possesses antitumor activity against squamous cell carcinoma and melanoma when used topically (Ogbourne et al. (2007) Anticancer Drugs. 18: 357; incorporated herein by reference).

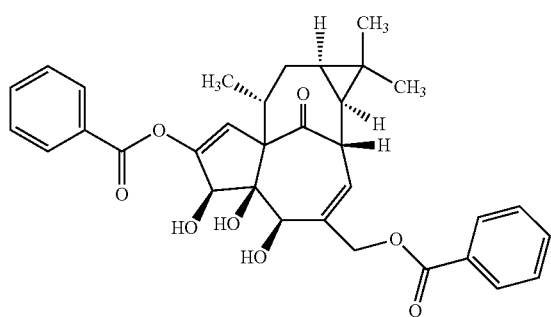 [SMILES: C[C@@H]1C[C@@H]2[C@H]([C@@H]3C=C(COC(=O)c4ccccc4)[C@@H](O)[C@]4(O)[C@@H](O)C(OC(=O)c5ccccc5)=CC14C3=O)C2(C)C]

Napthalenesulfonamides, including N-(n-heptyl)-5-chloro-1-naphthalenesulfonamide (SC-10) and N-(6-Phenylhexyl)-5-chloro-1-naphthalenesulfonamide, are members of another class of PKC activators. SC-10 activates PKC in a calcium-dependent manner, using a mechanism similar to that of phosphatidylserine (Ito et al. (1986) Biochemistry 25: 4179; incorporated herein by reference). Naphthalenesulfonamides act by a different mechanism from bryostatin and would be expected to show a synergistic effect with bryostatin or a member of another class of PKC activators. Structurally, naphthalenesulfonamides are similar to the calmodulin (CaM) antagonist W-7, but are reported to have no effect on CaM kinase.

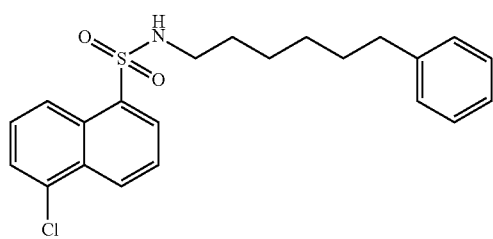 [SMILES: O=S(=O)(NCCCCCCc1ccccc1)c1cccc2c(Cl)cccc12]

The linoleic acid derivative DCP-LA (2-[(2-pentylcyclopropyl)methyl]cyclopropaneoctanoic acid) is one of the few known isoform-specific activators of PKC known. DCP-LA selectively activates PKCε with a maximal effect at 100 nM. (Kanno et al. (2006) *J. Lipid Res.* 47: 1146). Like SC-10, DCP-LA interacts with the phosphatidylserine binding site of PKC, instead of the diacylglycerol binding site.

An alternative approach to activating PKC directly is to increase the levels of the endogenous activator, diacylglycerol. Diacylglycerol kinase inhibitors such as 6-(2-(4-[(4-fluorophenyl)phenylmemylene]-1-piperidinyl)ethyl)-7-methyl-5H-thiazolo[3,2-a]pyrimidin-5-one (R59022) and [3-[2-[4-(bis-(4-fluorophenyl)methylene]piperidin-1-yl) ethyl]-2,3-dihydro-2-thioxo-4(1H)-quinazolinone (R59949) enhance the levels of the endogenous ligand diacylglycerol, thereby producing activation of PKC (Meinhardt et al. (2002) *Anti-Cancer Drugs* 13: 725).

Growth factor activators, such as the 4-methyl catechol derivatives, such as 4-methylcatechol acetic acid (MCBA), that stimulate the synthesis and/or activation of growth factors such as NGF and BDNF, also activate PKC as well as convergent pathways responsible for synaptogenesis and/or neuritic branching.

F. Fibroblast Growth Factor 18 (FGF-18)

Fibroblast Growth Factors ("FGF") are among the proteins that play vital roles in controlling embryonic development, cell growth, morphogenesis, and tissue repair in animals. (Hu et al. (1999) *Oncogene*, 18 (16): 2635-42). FGF-18 is one member of this family of proteins; it is a peptide consisting of 207 amino acids, encoded by a single memory related gene associated with spatial learning. It is expressed primarily in the lungs and kidneys and at lower levels in the heart, testes, spleen, skeletal muscle, and brain. (Hu et al. (1998) *Molecular Cellular Biology*, 18(10): 6063-6074). Sequence comparison studies indicated that FGF-18 is highly conserved between humans and mice and is most homologous to FGF-8 among the FGF family members. In continuing studies investigating the full role of FGF-18 in cellular and tissue development, FGF-18 has thus far been identified as a signaling molecule for proliferation in the adult lung and developing tissue, and it has been linked to cancerous cells.

The present invention contemplates the use of FGF-18, modified forms of FGF-18 and fragments of FGF-18 that each maintain the ability to improve learning an memory as described in U.S. Provisional Application Ser. No. 60/429,321 and PCT/IB03/05408, which are both incorporated by reference herein in their entireties.

All books, articles, patents or other publications and references are hereby incorporated by reference in their entireties. Reference to any compound herein includes the racemate as well as the single enantiomers.

EXAMPLES

The following Examples serve to further illustrate the present invention and are not to be construed as limiting its scope in any way.

Example 1: Open-Space-Swimming Test for Depression

Adult Wistar rats (180-200 g) were housed in a temperature-controlled (20-24° C.) room for at least a week prior to experimentation, allowed free access to food and water, and kept on a 12-h light/dark cycle. They were randomly assigned to different groups (eight each) and were moved to the test room in their home cages at least 1 h before trials. Rats were individually placed into a round pool with a diameter of 152 cm and height of 60 cm and was filled with 40 cm $H_2O$ (22±1° C.). The room and pool are part of the started set-up used for spatial water maze task. (Sun et al. (2002) *J. Pharmacol. Exp. Ther.* 300: 408-416). The tests for different drug treatment and control groups were in a counterbalanced order. No escape was available in these trials. Rats were free to swim (or not to swim) for 15 min and then removed and returned to their home cage after drying. Observers were obscured from sight of the rats during the trials, but were able to observe the animals' behaviors on a video screen monitor during trials. The same procedure (15 min session per day) was repeated 24 h later and continued for 3 additional days. Drugs were dissolved in a saline solution for test groups and saline alone was used in the control groups. Imipramine (10 mg/kg×3 day, i.p.), iproniazid (10 mg/kg×3 per day, i.p.), mianserin (10 mg/kg×3 per day, i.p.), alaproclate (10 mg/kg×3 per day), or saline were administered between the swimming trial sessions at 23, 2, and 1 h before the second, third, and fourth trial sessions, respectively. The rationale for the three doses before test trials is the more consistent predictive effects than those of a single dose (Porsolt et al. (1977) *Nature* 266: 730-730-732; Porsolt et al. (1978) *Eur. J. Pharmacol.* 47: 379-391; Poncelet et al, (1986) *Psychopharmacology* 90: 139-141). The swimming/drifting path was recorded with a video-tracking system that was also used for the spatial water maze task in other studies (Sun et al., 2002; Sun and Alkon, 2002a). The system tracks the animal's position by recording sequential x/y-coordinates of trigger events (video signal above track level) and calculating the distance, in the pool (sample period: 0.055 s) and adds the distance at pre-set intervals (15 min) during each trial. The tracking system, however, neither distinguishes nor determines the duration of any period of mobility or immobility. To evaluate whether the distance moved, as recorded by the tracking system, reflects the duration of active swimming, the investigator(s) also recorded the duration of active swimming on-line via the video screen monitor for a direct comparison of the two parameters.

Example 2. Open Space Swimming Test Induces Immobility in Rats

The rats injected with saline (eight per group) showed a gradual and significant reduction (FIG. 1) in mobility (distance moved) ($F_{3,31}$=49.717; P<0.001). The distance moved includes all the distance moved during the entire 15 min, as caused by active swimming/searching as well as slow drifts, which were caused by apparently non-searching movement of the legs, in the overall movement. Active swimming is defined as when a rat is making active swimming motions as those to move around in the pool. Unlike the behavior patterns reported in the forced swimming test (e.g. Rénéric et al., 2002), no climbing on the wall was observed, probably due to the large space available to the rats. As the trials progressed, the control rats showed progressively less and briefer intermittent periods of active swimming. A maximal reduction in their mobility was reached at the $3^{rd}$ trial in these control rats (FIG. 1). Typically, a control rat did not make any movements other than those just sufficient to keep its head above the water surface (immobility; not shown), a characteristic behavior that is taken as an indicator of depression in the forced swimming test.

Example 3. Induced Immobility Sensitivity to Traditional Antidepressant Treatments Treatment with antidepressants significantly decreased the reduction in the distance moved over trials (FIG. 1), compared with that of the control group. Statistical analysis revealed significant effects of groups ($F_{3,16}$=25,071; P<0.001) indicating that the mobility in rats that were injected with the antidepressants was significantly higher than that of the rats that were injected with vehicle only. These rats showed more and long lasting periods of active swimming/searching, measured as the distance swum, although the periods of active swimming were not quantified individually in the study. Moreover, a post hoc analysis revealed a significant difference from the $2^{nd}$ trial to the $4^{th}$ trial (P<0.05), confirming higher mobility of the rat groups that received the antidepressant treatment. For the three drug groups, statistical analysis revealed no significant intergroup difference ($F_{2,12}$=4.199; P<0.05), although iproniazid appeared more effective at the dose given than mianserin and imipramine in reducing the immobility. (FIG. 1). A comparison between the present results and previously reported data obtained by using the forced swimming test reveals that the present test shows an improved antidepressant effect in general.

Example 4. Induced Immobility Sensitivity to SSRI-Antidepressant Treatment

Figure 2:
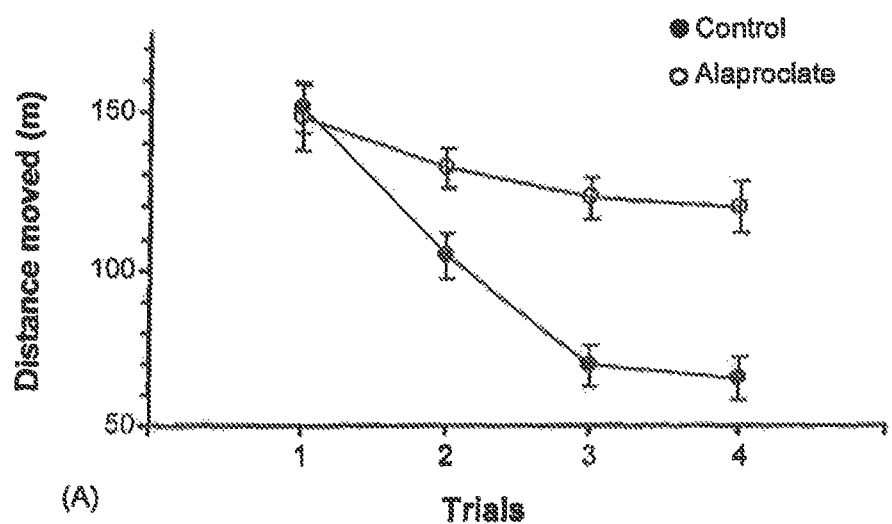
FIG. 2 depicts the effect of alaproclate on the mobility (distance moved) (A) and duration of active swimming of rats (B) in the open-space-swimming test.
Figure 2:
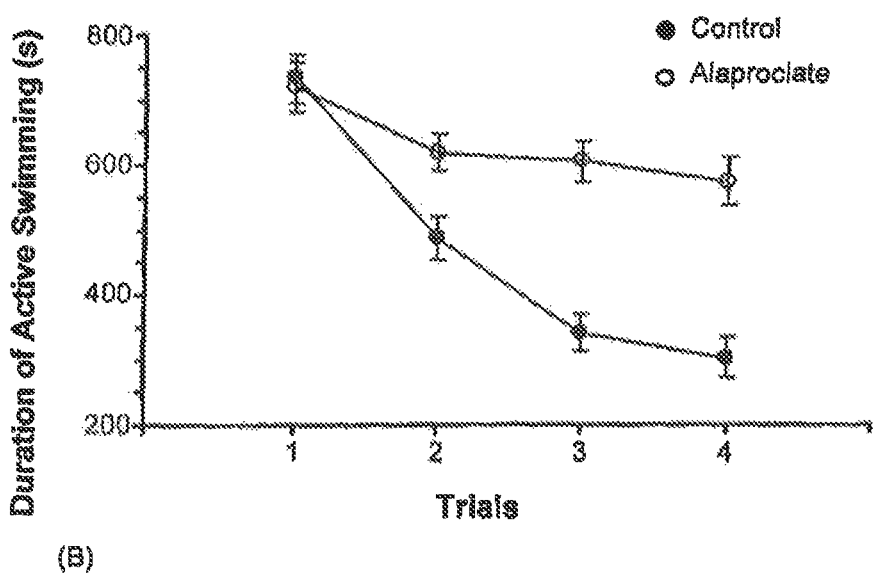

Alaproclate, an SSRI, was effective in reducing the immobility in the open space swimming test (FIG. 2A), as compared with that of a control group. Statistical analysis yielded a significant difference between the groups ($F_{1,8}$=32.60; P<0.001) indicating that the mobility of the rats that were injected with alaproclate was significantly higher than that of the rats that were injected with vehicle only.

Whether the observed difference in the distance moved would reflect different duration of active swimming was evaluated by recording the periods during which the rats were clearly performing active swimming, i.e., making those obvious movements to swim around in the pool. A comparison of the results of the different groups was illustrated in FIG. 2B. The duration of active swimming of the alaproclate group was significantly longer (group difference: $F_{1,8}$=31.51; P<0.001) than that of the control group. The % change in distance moved (using corresponding change of the control group as 100%) did not significantly differ (P>0.05, unpaired test) from the % change in the duration of active swimming (using corresponding change of the control group as 100%). Thus, the results show that the parameter, "distance moved", indeed reflects duration of mobility during the test.

Example 5: Induced Immobility Sensitivity to Phenylalanine

Depressive behavior in rats was induced by placing the animals in an open-space swimming apparatus, as described herein, for 15 minutes per trial per day. The animals were subjected to three trials over the course of three days. The animals were divided into three groups: control rats (8); phenylalanine rats (10); and imipramine rats (10). The control rats received a single i.v. dose of saline in the tail vein, 3.5 hours before the second trial. Rats in the bryostatin-1 group received a single i.v. dose of phenylalanine in the tail vein, 3.5 hours before the second trial. Rats in the imipramine group received 3 i.p. doses (10 mg/kg) at 23, 2 and 1 hour before the first, second and third trials, respectively.

Figure 3:
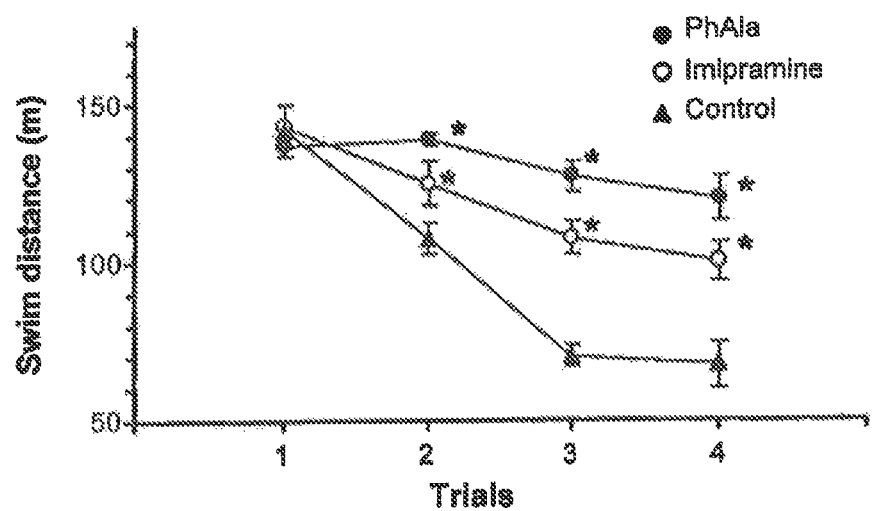
FIG. 3 compares the effect of imipramine and the carbonic anhydrase activator, phenylalanine, on the mobility of rats in the open-space-swimming test.

Phenylalanine, a carbonic anhydrase activator, was effective in reducing the immobility in the open-space-swimming test, as compared with a control group and a group treated with the antidepressant imipramine. (FIG. 3). Statistical analysis demonstrates a significant difference between the phenylalanine, imipramine and control groups, thereby indicating that the mobility of the rats injected with phenylalanine is significantly higher than that of the rats receiving either imipramine or saline.

Example 6: Induced Immobility Sensitivity to Bryostatin-1

Depressive behavior in rats was induced by placing the animals in an open-space swimming apparatus, as described herein, for 15 minutes per trial per day. The animals were subjected to three trials over the course of three days. The animals were divided into three groups: control rats (8); bryostatin-1 rats (10); and imipramine rats (10). The control rats received a single i.v. dose of saline in the tail vein, 3.5 hours before the second trial. Rats in the bryostatin-1 group received a single i.v. dose of bryostatin-1 (80 (µg/kg) in the tail vein, 3.5 hours before the second trial. Rats in the imipramine group received 3 i.p. doses (10 mg/kg) at 23, 2 and 1 hour before the first, second and third trials, respectively.

Figure 4:
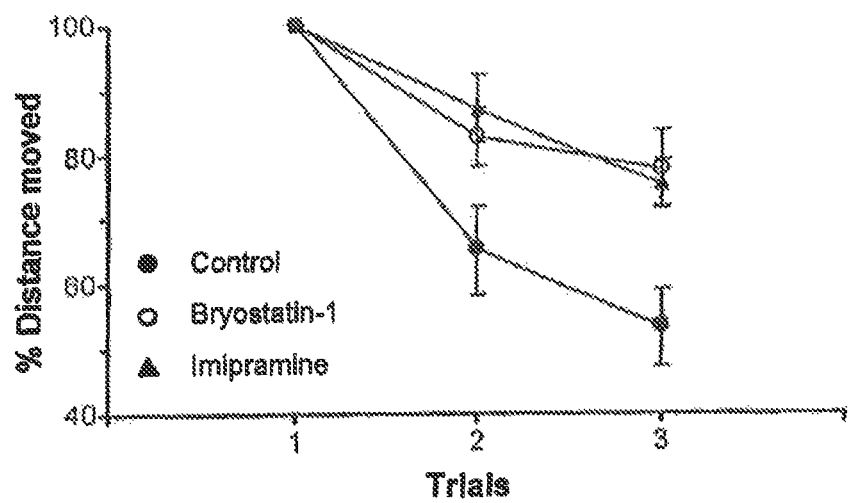
FIG. 4 compares the effect of imipramine and the PKC activator, bryostatin-1, on the mobility of rats in the open-space-swimming test.

Bryostatin-1, a PKC activator, was effective in reducing immobility in the open-space-swimming test, as compared with a control group and a group treated with the antidepressant, imipramine. (FIG. 4). Statistical analysis demonstrates a significant difference between the phenylalanine, imipramine and control groups, thereby indicating that the mobility of the rats injected with bryostatin-1 is significantly higher than that of the rats receiving either imipramine or saline ($F_{2,27}$=6.168; P=0.007). No significant difference was observed between the bryostatin-1 and imipramine groups ($F_{2,27}$=10.128; P=0.724).

Example 7: Induced Immobility Sensitivity to Imidazole

Imidazole, a carbonic anhydrase activator, is effective in reducing immobility in the open-space-swimming test when compared with a control group and a group treated with the antidepressant imipramine.

Example 8: Induced Immobility Sensitivity to Linked Diimidizole

Linked diimidazole (structure III, wherein $R_2$ is H and n=1 or 2), a carbonic anhydrase activator, is effective in reducing immobility in the open-space-swimming test when compared with a control group and a group treated with the antidepressant imipramine.

Example 9: Induced Immobility Sensitivity to Tyrosine

Tyrosine, a carbonic anhydrase activator, is effective in reducing immobility in the open-space-swimming test when compared with a control group and a group treated with the antidepressant imipramine.

Example 10: Induced Immobility Sensitivity to 4-fluoro-phenylalanine

[4-Fluoro-phenylalanine a carbonic anhydrase activator, is effective in reducing immobility in the open-space-swimming test when compared with a control group and a group treated with the antidepressant imipramine.

Example 11: Induced Immobility Sensitivity to Carbonic Anhydrase Activators that Provide Carbonic Anhydrase Activity of Between 150 and 250% that Observed with Alanine Compounds that activate carbonic anhydrase II between 150 and 250% relative to the activation observed for alanine, are effective in reducing immobility in the open-space-swimming test when compared with a control group and a group treated with the antidepressant imipramine.

Example 12: Induced Immobility Sensitivity to Neristatins

Neristatins, PKC activators, are effective in reducing immobility in the open-space-swimming test when compared with a control group and a group treated with the antidepressant imipramine.

Example 13: Induced Immobility Sensitivity to FGF-18

FGF-18, a PKC activator, is effective in reducing immobility in the open-space-swimming test when compared with a control group and a group treated with the antidepressant imipramine.

We claim:

1. A method of treating depression in a subject in need thereof, comprising administering an effective amount of a composition comprising a protein kinase C (PKC) activator and a pharmaceutically acceptable carrier, wherein the PKC activator is chosen from FGF-18, octylindolactam V, neristatins, bryologs, 1,2-sn-diacylglycerols having unsaturated fatty acids, farnesyl thiotriazole, iripallidal, 2-[(2-pentylcyclopropyl)methyl]-cyclopropaneoctanoic acid, growth factor activators chosen from 4-methylcatechol derivatives, daphnane-type diterpenes chosen from gnidimacrin, ingenol, ingenol 3,20-dibenzoate, and ingenol-3-angelate, napthalenesulfonamides chosen from N-(n-heptyl)-5-chloro-1-napthalenesulfonamide and N-(6-Phenylhexyl)-5-chloro-1-naphthalenesulfonamide, diacylglycerol kinase inhibitors chosen from 6-(2-(4-[(4-fluorophenyl)phenylmethylene]-1-piperidinyl)ethyl)-7-methyl-5H-thiazolo[3,2-a]pyrimidin-5-one and [3-[2-[4-(bis-(4-fluorophenyl)methylene]piperidin-1-yl)ethyl]-2,3-dihydro-2-thioxo-4(1H)-quinazolinone, and a combination thereof.

2. The method of claim 1, wherein the bryologs are chosen from B-ring bryologs and A-ring bryologs.

3. The method of claim 1, wherein the bryolog is a compound with a formula:

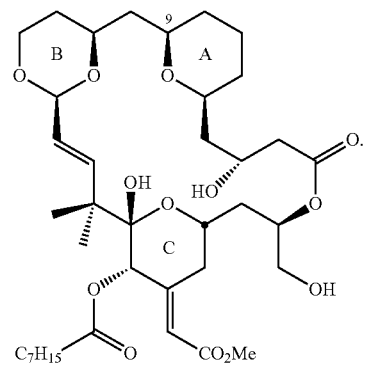

4. The method of claim 1, wherein the bryolog is a compound with a formula:

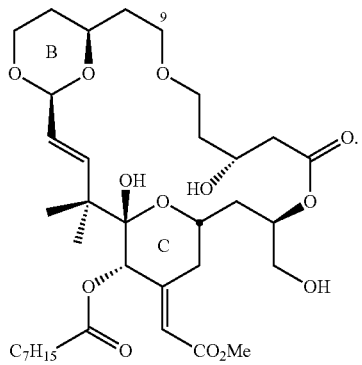

5. The method of claim 2, wherein the B-ring byrologs are chosen from

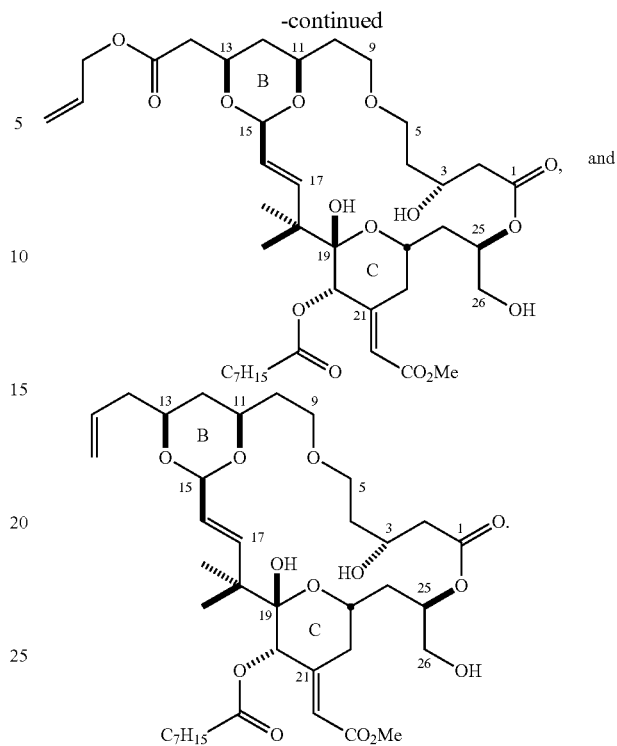

6. The method of claim 2, wherein the A-Ring bryologs are chosen from wherein R is t-Bu, Ph, or $(CH_2)_3$p-Br-Ph.

7. The method of claim 1, wherein the unsaturated fatty acids are cis-unsaturated fatty acids.

8. The method of claim 1, wherein the 4-methylcatechol derivative is 4-methylcatechol acetic acid.

9. The method of claim 1, wherein the neristatin is neristatin-1.

* * * * *